United States Patent [19]

Cayre

[11] Patent Number: 5,180,819

[45] Date of Patent: Jan. 19, 1993

[54] PURIFIED MYELOBLASTIN, NUCLEIC ACID MOLECULE ENCODING SAME, AND USES THEREOF

[75] Inventor: Yvon Cayre, New York, N.Y.

[73] Assignee: The Trustees of Columbia University in the City of New York, New York, N.Y.

[21] Appl. No.: 455,614

[22] Filed: Dec. 22, 1989

[51] Int. Cl.[5] ............... C07H 15/12; C07K 3/00; C12Q 1/68; A61K 37/00

[52] U.S. Cl. ..................... 536/23.2; 530/350; 530/387.9; 530/388.26; 435/6; 435/69.1

[58] Field of Search ............ 435/5, 6, 69.1, 172.1; 536/27, 28, 29; 514/12, 44; 530/350, 387

[56] References Cited

U.S. PATENT DOCUMENTS 4,795,700  1/1989  Dervan et al. ..................... 435/5

OTHER PUBLICATIONS

Bories et al. (1989) Cell, vol. 59, pp. 959–968.
Cayre et al. (1987) PNAS vol. 84, pp. 7619–7623.
Solomon et al. (1988) PNAS, vol. 85, pp. 6904–6908.
Koeffler (1983) Blood, vol. 62, pp. 709–721.
Takahashi et al. (1988, Feb.), JBC, vol. 263, pp. 2543–2547.
Holt et al. (1988, Feb.), Molecular and Cellular Biology, vol. 8, pp. 963–973.
Agrawal, S., et al., Proc. Natl. Acad. Sci. USA, vol. 86, pp. 7790–7794 (1989) (Exhibit A).
Heikkila, R., et al., Nature, vol. 328, pp. 445–449 (1987) (Exhibit D).
Wickstrom, E., et al., In Vitro Cellular & Developmental Biology, vol. 24, pp. 297–302 (1989) (Exhibit G).
Wickstrom, E., et al., Proc. Natl. Acad. Sci. USA, vol. 85, pp. 1028–1032 (1988) (Exhibit H).

Primary Examiner—David L. Lacey
Assistant Examiner—Gian P. Wang
Attorney, Agent, or Firm—John P. White

[57] ABSTRACT

This invention provides an isolated nucleic acid molecule encoding human myeloblastin, a nucleic acid probe for detecting myeloblastin, and an antisense oligodeoxynucleotide complementary to myeloblastin mRNA. The invention also provides antibodies directed to myeloblastin, and purified myeloblastin. The invention further provides a pharmaceutical composition to inhibit proliferation and induce differentiation of leukemia cells, a myeloblastin inhibitor, and a factor suppressing myeloblastin expression. The invention provides methods for identifying leukemia cells which express different quantities of myeloblastin, treating leukemia, and for preparing purified myeloblastin.

13 Claims, 26 Drawing Sheets

```
     -66
     TGA GCG GTG CTG CCC GAG CTG CGG AGA TCG TGG GCG GGC ACG AGC GCA 1                        20
     GGC ACA CTC CCG CCC TAC ATG GCC TCC CTG CAG ATG CGG GGG AAC CCG
                             Met Ala Ser Leu Gln Met Arg Gly Glu Asn Pro 40                        60
     GGC AGC CAC TTC TGC GGA GGC ACC TTG ATC CAC CCC AGC TTC GTG CTG
     Glu Ser His Phe Cys Glu Glu Thr Leu Ile His Pro Ser Phe Val Leu 80                       100                       120
     ACG GCC GCG CAC TGC CTG CGG GAC ATA CCC CAG CGC CTG GTG AAC GTG
     Thr Ala Ala His Cys Leu Arg Asp Ile Pro Glu Arg Leu Val Asn Val
                      *
                         140                       160
     GTG CTC GGA GCC CAC AAC GTG CGG ACG CAG GAG CCC ACC CAG CAG CAC
     Val Leu Gly Ala His Asn Val Arg Thr Gln Glu Pro Thr Gln Gln His 180                       200                       220
     TTC TCG GTG GCT CAG GTG TTT CTG AAC AAC TAC GAC GCG GAG AAC AAA
     Phe Ser Val Ala Gln Val Phe Leu Asn Asn Tyr Asp Ala Glu Asn Lys 240                       260
     CTG AAC GAC ATT CTC CTC ATC CAG CTG AGC AGC CCA GCC AAC CTC AGT
     Leu Asn Asp Ile Leu Leu Ile Gln Leu Ser Ser Pro Ala Asn Leu Ser
                 *
                     280                       300
     GCC TCC GTC ACC TCA GTC CAG CTG CCA CAG CAG GAC CAG CCA GTG CCC
     Ala Ser Val Thr Ser Val Gln Leu Pro Gln Gln Asp Gln Pro Val Pro 320                       340                       360
     CAG GGC ACC CAG TGC CTG GCC ATG GGC TGG GGC CGG GTG GGT GCC CAC
     His Gly Thr Gln Cys Leu Ala Met Gly Trp Gly Arg Val Gly Ala His 380                       400
     GAC CCC CCA GCC CAG GTC CTG CAG GAG CTC AAT GTC ACC GTG GTC ACC
     Asp Pro Pro Ala Gln Val Leu Gln Glu Leu Asn Val Thr Val Val Thr 420                       440                       460
     TTC TTC TGC CGG CCA CAT AAC ATT TGC ACT TTC GTC CCT CGC CGC AAG
     Phe Phe Cys Arg Pro His Asn Ile Cys Thr Phe Val Pro Arg Arg Lys
```

Figure 1B

U937
U937+PMA
KG-1
K562

28S—

18S—

—$\beta_2$-m

```
-66
TGA GCG GTG CTG CCC GAG CTG CGG AGA TCG TGG GCG GGC ACG AGC GCA
                                                  20
GGC ACA CTC CCG CCC TAC ATG GCC TCC CTG CAG ATG CGG GGG AAC CCG
                              1   Met Ala Ser Leu Gln Met Arg Glu Asn Pro
                                                  60
GGC AGC CAC TTC TGC GGA GGC ACC TTG ATC CAC CCC AGC TTC GTG CTG
Glu Ser His Phe Cys Gly Glu Thr Leu Ile His Pro Ser Phe Val Leu
                                                  120
     100
ACG GCC GCG CAC TGC CTG CGG GAC ATA CCC CAG CGC CTG GTG AAC GTG
Thr Ala Ala His Cys Leu Arg Asp Ile Pro Gln Arg Leu Val Asn Val
             *
                    140                              160
GTG CTC GGA GCC CAC AAC GTG CGG ACG CAG GAG CCC ACC CAG CAG CAC
Val Leu Gly Ala His Asn Val Arg Thr Gln Glu Pro Thr Gln Gln His
     180                                        200           220
TTC TCG GTG GCT CAG GTG TTT CTG AAC AAC TAC GAC GCG GAG AAC AAA
Phe Ser Val Ala Gln Val Phe Leu Asn Asn Tyr Asp Ala Glu Asn Lys
```

Figure 1D(2)

```
                                          240                                       260
CTG AAC GAC ATT CTC CTC ATC CAG CTG AGC AGC CCA GCC AAC CTC AGT
Leu Asn Asp Ile Leu Leu Ile Gln Leu Ser Ser Pro Ala Asn Leu Ser
        *
              280                                 300
GCC TCC GTC ACC TCA GTC CAG CTG CCA CAG GAC CAG CCA GTG CCC
Ala Ser Val Thr Ser Val Gln Leu Pro Gln Asp Gln Pro Val Pro
                                  340                               360
CAG GGC ACC CAG TGC CTG GCC ATG GGC TGG GGC CGG GTG GGT GCC CAC
Gln Gly Thr Gln Cys Leu Ala Met Gly Trp Gly Arg Val Gly Ala His
                        380                             400
GAC CCC CCA GCC CAG GTC CTG CAG GAG CTC AAT GTC ACC GTG GTC ACC
Asp Pro Pro Ala Gln Val Leu Gln Glu Leu Asn Val Thr Val Val Thr
        420                             440                         460
TTC TTC TGC CGG CCA CAT AAC ATT TGC ACT TTC GTC CCT CGC CGC AAG
Phe Phe Cys Arg Pro His Asn Ile Cys Thr Phe Val Pro Arg Arg Lys
```

Figure 1D(3)

```
                                            480                                  500
GCC GGC ATC TGC TTC GGA GAC TCA GGT GGC CCC CTG ATC TGT GAT GGC
Ala Gly Ile Cys Phe Gly Asp Ser Gly Gly Pro Leu Ile Cys Asp Gly
                                    *
              520                                  540
ATC ATC CAA GGA ATA GAC TCC TTC GTG ATC TGG GGA TGT GCC ACC CGC
Ile Ile Gln Gly Ile Asp Ser Phe Val Ile Trp Gly Cys Ala Thr Arg 560                                  580                                  600
CTT TTC CCT GAC TTC TTC ACG CGG GTA GCC CTC TAC GTG GAC TGG ATC
Leu Phe Pro Asp Phe Phe Thr Arg Val Ala Leu Tyr Val Asp Trp Ile 620                                  640
CGT TCT ACG CTG CGC CGT GTG GAG GCC AAG GGC CGC CCC TGA ACC GCC
Arg Ser Thr Leu Arg Arg Val Glu Ala Lys Gly Arg Pro 660                                  680                       700
CCT CCC ACA GCG CTG GCC GGG ACC CCG AGC CTG GCT CCA AAC CCT CGA

720
GGC GGA TCT TTG GAC AGA AGC TCT TG
```

Figure 1E(1)

```
                                                           1
Myeloblastin        . . . . . . . . . . . . . . . . . . .  M A S L Q M
Neutrophil elastase I V G G R R A R P H A W P F M . V S L Q L
                    1                                     20

0  24  48  96
Hours

Figure 2E(1)
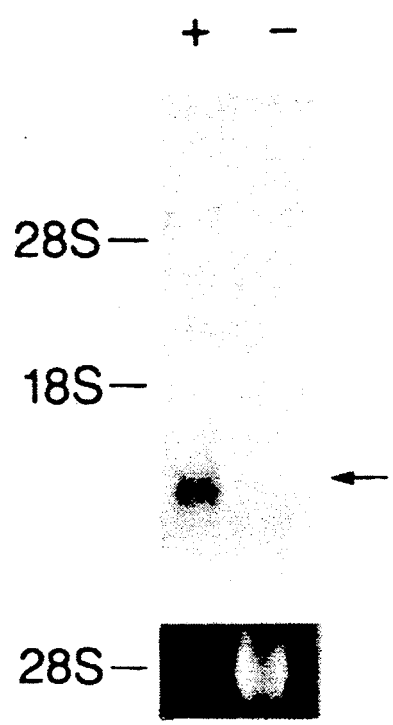

Figure 2E(2)
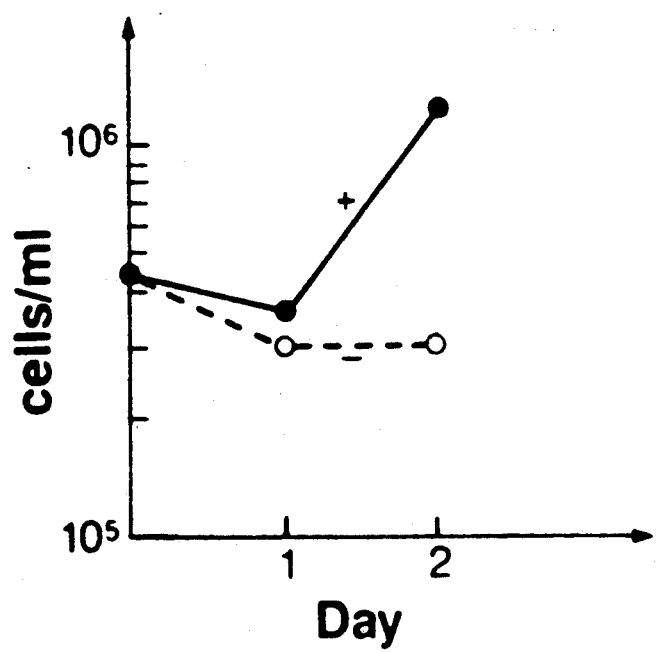

Figure 3A kDa
200-

97-

68-

43-

29- ■ • Mb 18-
ni   i

Figure 3D kDa
200—

PURIFIED MYELOBLASTIN, NUCLEIC ACID MOLECULE ENCODING SAME, AND USES THEREOF

The invention described herein was made in the course of work under Grant No. RO1CA43225 from the National Institutes of Health, U.S. Department of Health and Human Services. The U.S. Government has certain rights in this invention.

BACKGROUND OF THE INVENTION

The promyelocyte-like leukemia cell line HL-60 can be induced to differentiate terminally in vitro. Treatment with agents such as dimethyl sulfoxide ($Me_2SO$) and retinoic acid (RA) results in the expression of a granulocytic phenotype (Collins, et al., 1977; Breitman, et al., 1980), while exposure to 1,25-dihydroxyvitamin $D_3$ (1,25-$(OH)_2D_3$) or phorbol 12-myristate 13-acetate (PMA) leads to the expression of a monocytic-macrophagic phenotype (Bar-Shavit, et al., 1983; Huberman and Callagham, 1979; McCarthy, et al., 1983; Rovera, et al., 1979). A common effect of all these inducers is that HL-60 cells undergo growth arrest while they terminally differentiate. A number of genes are known to be regulated during HL-60 differentiation: c-fms is induced when cells differentiate along the monocyte-macrophage pathway (Sariban, et al., 1985); c-fos is rapidly induced by PMA but not by 1,25-$(OH)_2D_3$, $Me_2SO$, and RA (Muller, et al., 1985); c-myc is down-regulated by PMA and 1,25-$(OH)_2D_3$ (Einat, et al., 1985; Reitsma, et al., 1983) as well as $Me_2SO$ and RA (Einat, et al., 1985; Westin, et al., 1982).

We have recently derived and analyzed a clonal variant of HL-60, 1F10, that permits us to study several intermediate steps in HL-60 differentiation (Cayre, et al., 1987). 1F10 cells treated with PMA or 1,25-$(OH)_2D_3$ are arrested at discrete steps in differentiation (Cayre, et al., 1987).

These cells are still blastic and resemble a promyelocyte. They are morphologically similar to the original HL-60 cells, grow exponentially, and do not exhibit phenotypic characteristics of differentiating cells. Complete maturation and growth arrest of the 1F10 cells are attained when 1,25-$(OH)_2D_3$ and PMA are used simultaneously. When the two inducers are added sequentially, cells must be treated first with 1,25-$(OH)_2D_3$ to fully differentiate (Cayre, et al., 1987). This and the study of genes such as c-myc (Reitsma, et al., 1983), pD3-137 (Solomon, et al., 1988), and c-fms (Sariban, et al., 1985), which are similarly regulated by 1,25-$(OH)_2D_3$ in both HL-60 and 1F10 cells, suggested that the 1,25-$(OH)_2D_3$-treated 1F10 cells are arrested at an immature step in differentiation (Cayre, et al., 1987; Solomon, et al., 1988).

To identify genes that are regulated at discrete steps in HL-60 differentiation, cDNA subtraction was applied to the 1F10 system (Solomon, et al., 1988). By this method, we have isolated a cDNA clone encoding a novel serine protease, myeloblastin. Myeloblastin mRNA is down-regulated by granulocytic and monocytic inducers of HL-60 differentiation. In the absence of inducer, myeloblastin mRNA is regulated by serum. We have used an antisense oligodeoxynucleotide to inhibit myeloblastin expression. This inhibition results in proliferation arrest and differentiation of the leukemic cells.

As shown by deduced amino acid sequence analysis and DFP (diisopropylfluorophosphate) labelling, myeloblastin is a serine protease. Because protease inhibitors affect the growth of normal and transformed cells, earlier investigators have proposed a role for proteases in the regulation of cell growth (Gibson, et al., 1984; Sullivan and Quigley, 1986). A series of cell surface-related proteolytic events involving serine proteases with thrombin-like activity are required for cell proliferation and differentiation (for review, see Carrell, 1988). These events are controlled by surface-associated inhibitors of serine proteases (Baker, et al., 1986). For example, one of the protease nexins has been identified as the natural factor that promotes the outgrowth of neurites from neuronal cells (Gloor, et al., 1986). More recently, other investigators have cloned a cDNA from HL-60 cells that has homology to members of a family of Kunitz-type serine protease inhibitors and that is also a potential promoter of neurite growth (Tanzi, et al., 1988; Carrell, 1988). These Kunitz-type inhibitors have specificity for several serine proteases including elastase (for review, see Carrell, 1988).

Myeloblastin shares amino acid sequence homology with HuNE (Human neutrophil elastase). Similar to myeloblastin mRNA, HuNE mRNA is expressed in both HL-60 and U937 cells (Takahashi, et al., 1988). As is the case for myeloblastin mRNA, the HuNE mRNA is down-regulated by PMA in HL-60 cells (Takahashi, et al., 1988). A major difference between HuNE and myeloblastin is that myeloblastin mRNA is down-regulated while HuNE mRNA is up-regulated when HL-60 cells are exposed to $Me_2SO$ (Takahashi, et al., 1988). The functional relevance, if any, of amino acid homologies between HuNE and myeloblastin is unclear at present.

Regulation of myeloblastin has similarities with regulation of c-myc. A remarkable feature of myeloblastin is that it is down-regulated by both monocytic and granulocytic inducers of HL-60 differentiation. This down-regulation by several inducers is consistent with the fact that this serine protease is associated with proliferation arrest—which always accompanies HL-60 differentiation (Collins, et al., 1977; Huberman and Callagham, 1979; Rovera, et al., 1979; Breitman, et al., 1980; Bar-Shavit, et al., 1983; McCarthy, et al., 1983)—and is reminiscent of the down-regulation of c-myc mRNA during differentiation of HL-60 cells. As is the case for myeloblastin mRNA, induced differentiation along either the granulocytic or the monocytic pathway results in a profound decrease in c-myc mRNA levels (Sariban, et al., 1985; Reitsma, et al., 1983; Westin, et al., 1982); c-myc is transcriptionally controlled by 1,25-$(OH)_2D_3$ (Simpson, et al., 1987) and is involved in cell proliferation (Kelly, et al., 1983; Kaczmarek, et al., 1985). As is the case for myeloblastin mRNA, c-myc mRNA is down-regulated at different times with different inducers (Reitsma, et al., 1983; Sariban, et al., 1985; Siebenlist, et al., 1988). The fact that myeloblastin mRNA is down-regulated at different times using different inducers is consistent with previous reports that showed that $Me_2SO$, PMA, retinoic acid, and 1,25$(OH)_2D_3$ at concentrations similar to those used in our study did not differentiate HL-60 cells at the same rate (Collins, et al., 1978; Rovera, et al., 1979; Breitman, et al., 1980; McCarthy, et al., 1983). The inhibition of c-myc expression by specific antisense oligodeoxynmucleotides oligodeoxynucleotides results in inhibition of proliferation and induction of differentiation of HL-60 cells (Heikkila, et al., 1987; Wickstrom, et al., 1988; Holt, et al., 1988).

Other genes that are regulated during HL-60 differentiation, such as c-myc and c-fos, can be induced in response to serum. Because myeloblastin mRNA is induced in response to serum stimulation of HL-60 cells, we propose that myeloblastin is a member of a restricted family of genes that are associated with proliferation and are regulated during HL-60 differentiation. Since reduction of c-myc expression may not be obligatory or sufficient for growth arrest to occur (Shen-Ong, et al., 1987; Cayre, et al., 1987), it will be of interest to know whether myeloblastin and c-myc are interdependent for controlling proliferation and differentiation of HL-60 cells. It will also be of interest to explore whether similar serum and transcription factors regulate both myeloblastin and c-myc expression.

Myeloblastin is a novel protein not disclosed in any earlier references. Detecting its expression in undifferentiated leukemia cells provides an improved means of determining whether the cells are lymphoblastic or monocytic. Also, levels of myeloblastin expression provide information about the onset and development of leukemia that is useful in prognosis.

In addition, the use of antisense oligonucleotides complementary to myeloblastin mRNA provide a therapeutic treatment for leukemia by down-regulating myeloblastin expression in leukemia cells, which results in a reversal of their abnormal behavior. This method represents a distinct improvement over chemotherapy in that it causes no damage to normal cells. Natural myeloblastin inhibitors for therapeutic use also have advantages over chemotherapy in specificity and safety. Wickstrom, et al, 1988 and 1989, disclose antisense oligonucleotides complementary to the oncogene c-myc, and Agrawal, et al., 1989, disclose antisense oligodeoxynucleotides complementary to HIV RNA. However, none of these references disclose antisense oligonucleotides complementary to myeloblastin mRNA.

SUMMARY OF THE INVENTION

This invention provides an isolated nucleic acid molecule encoding myeloblastin, in particular human myeloblastin.

This invention provides an oligonucleotide of at least about 10 nucleotides in length having a sequence complementary or identical to a sequence included within the sequence shown in FIG. 1D.

This invention also provides a purified polypeptide having substantially the same amino acid sequence as shown in FIG. 1D and having the biological activity of human myeloblastin.

This invention also provides an antibody directed to an epitope present on human myeloblastin.

This invention provides a pharmaceutical composition comprising an amount of an antisense oligonucleotide complementary to human myeloblastin mRNA effective to inhibit proliferation and induce differentiation of leukemia cells.

This invention provides a molecule that inhibits the protease activity of myeloblastin and a factor that suppresses the transcription of myeloblastin by binding to the promoter of the myeloblastin gene so as to prevent the transcription of myeloblastin mRNA.

This invention provides a method for identifying a leukemia cell expressing myeloblastin which comprises contacting the cell with a nucleic acid probe for myeloblastin under conditions which permit the probe to hybridize with mRNA encoding myeloblastin if any such is present, and detecting expression by detecting any hybridization which occurs.

This invention provides a method for inhibiting proliferation and inducing differentiation of a leukemia cell which comprises contacting the leukemia cell with an antisense oligonucleotide complementary to human myeloblastin mRNA so as to allow hybridization of the oligonucleotide to myeloblastin mRNA in the cell, thereby preventing translation of myeloblastin mRNA and production of myeloblastin, resulting in inhibition of proliferation and induced differentiation of the leukemia cell.

This invention provides a method of treating a subject with leukemia comprising contacting the affected cells with an amount of an antisense oligonucleotide complementary to human myeloblastin mRNA effective to inhibit their proliferation and induce their differentiation.

This invention also provides a method of treating a subject with leukemia which comprises administering to the subject an amount of a pharmaceutical composition comprising an antisense oligonucleotide complementary to human myeloblastin mRNA effective to inhibit proliferation and induce differentiation of leukemia cells, a carrier, a stabilizing substance, and a tracing substance.

This invention provides a method of determining whether a molecule is effective as an inhibitor of myeloblastin activity in leukemia cells which comprises propagating leukemia cells in a mouse with severe combined immunodeficiency, injecting the protein into the mouse, and determining whether the protein is effective as an inhibitor of myeloblastin activity by determining whether the mouse is cured of leukemia.

This invention provides a method of treating a subject with leukemia which comprises propagating the subject's bone marrow cells in a mouse with severe combined immunodeficiency and determining whether a protein will inhibit myeloblastin activity in that subject by injecting the protein into the mouse, and determining whether the protein is effective as an inhibitor of myeloblastin activity in that subject by determining whether the mouse is cured of leukemia.

This invention provides a method of preparing purified myeloblastin which comprises homogenizing human cells that express myeloblastin, isolating serine proteases from the resulting homogenate using an affinity column comprising a serine protease inhibitor which binds to serine proteases in the homogenate, running the resulting serine proteases over an FPLC column and isolating the resulting fractions, purifying the resulting fractions by contacting them with an ion exchange column, and determining which fraction contains myeloblastin by contacting each fraction with an antibody directed to an epitope on myeloblastin and determining whether the myeloblastin in the fraction binds to the antibody. An example of a human cell is a human leukemia cell, such as an HL-60 cell or a cell of the 1F10 cell system.

This invention further provides a method of preparing purified human myeloblastin which comprises cloning an isolated nucleic acid molecule encoding myeloblastin, such as a DNA or cDNA molecule, into an expression vector comprising a promoter and a fusion gene, transfecting a suitable host cell with the resulting expression vector and propagating the host in a suitable culture medium so that that a myeloblastin fusion protein consisting of myeloblastin and the fusion gene product are produced by the host cell, and isolating myeloblastin from the resulting culture medium by contacting the culture medium with an affinity column to which the fusion gene product binds to isolate the myeloblastin fusion protein and cleaving off the fusion gene product to produce myeloblastin.

Figure 1A:
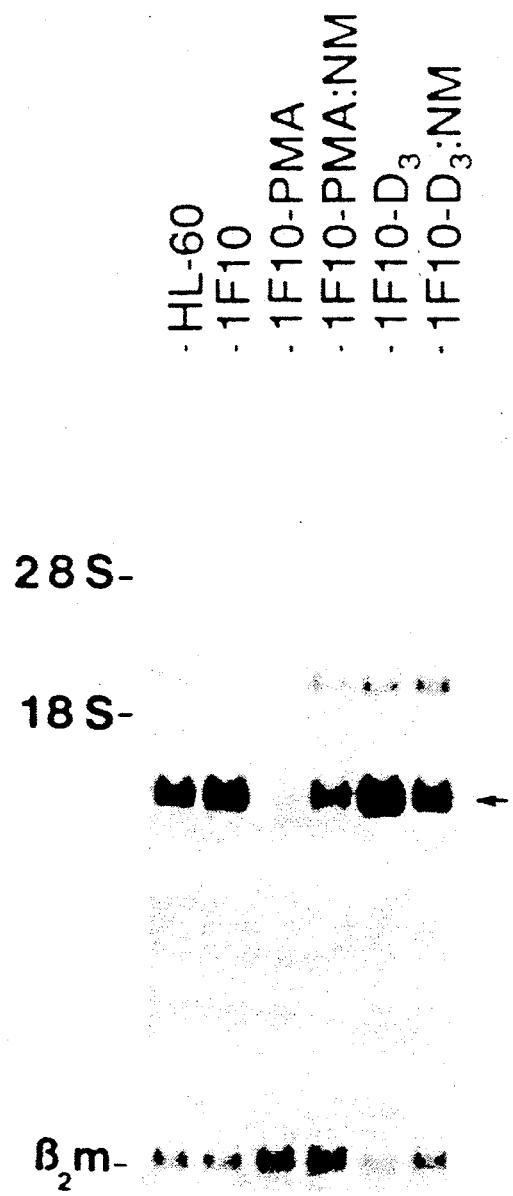
FIG 1

Cell Distribution of Myeloblastin mRNA in Various Human Leukemia Cell Lines and Primary Structural Analysis FIG. 1A Autoradiogram of myeloblastin mRNA in both HL-60 and 1F10 cells. 1F10-PMA and 1F10-D3 cells are 1F10 cells permanently treated with PMA (107 nM) and 1,25-$(OH)_2D_3$ (0.6 $\mu$M), respectively. 1F10-PMA:NM and 1F10-D3:NM are respectively, 1F10-PMA and 1F10-D3 cells cultured for 15 days in inducer-free medium.

FIG. 1B Autoradiogram of myeloblastin mRNA in U937 (before and after treatment with PMA [107 nM]), KG-1, and K562 cells.

FIG. C RNA blot analysis of HL-60 and human PBMs.

Figure 1C:

FIGS. 1A and 1B, bottom panel show the same blot hybridized with a $\beta_2$-microglobulin ($\beta_2$-m) nick-translated cDNA probe for assessment of RNA quantities in each lane. In FIG. 1C, the lower part is ethidium bromide-stained 28S rRNA from the gel prior to transfer. In FIGS. 1A, 1B, and 1C, 28S and 18S ribosomal RNA are indicated as size markers, and arrows indicate the position of myeloblastin mRNA.

FIGS. 1D and 1E show primary structural analysis of myeloblastin cDNA clones and relatedness to the HuNE gene.

FIG. 1D Nucleotide sequence and predicted amino acid sequence of myeloblastin. The deduced amino acid sequence of the open reading frame is displayed below the nucleotide sequence. Numbers above the nucleotide sequence of the strand corresponding to the mRNA refer to the position of the nucleotide. The TGA termination codon is underlined. At position −66, a nonsense codon is also underlined. The amino acids that form the catalytic triad of the serum proteases (His-30, Asp-77, and Ser-162) are marked by asterisks.

FIG. 1E Amino acid homology between myeloblastin and HuNE. The two sequences are maximally aligned. Numbers on each line refer to the positions of the amino acid homology between myeloblastin and HuNE. Amino acids that are identical are boxed. The amino acids that form the catalytic triad of the serine proteases are marked by asterisks. The N-linked glycosylation sites of HuNE as well as the putative N-linked glycosylation sites at Asn-88 and Asn-133 on myeloblastin are indicated by dots. Plus signs indicate the eight conserved cysteines, which are expected to form disulfide bonds: Cys-15-Cys-31, Cys-111-Cys-168, Cys-141-Cys-147, and CyS-158-Cys-183. The caret indicates the putative cleavage site of the propeptide in HuNE.

FIG. 2

Figure 1C:
Figure 2A:
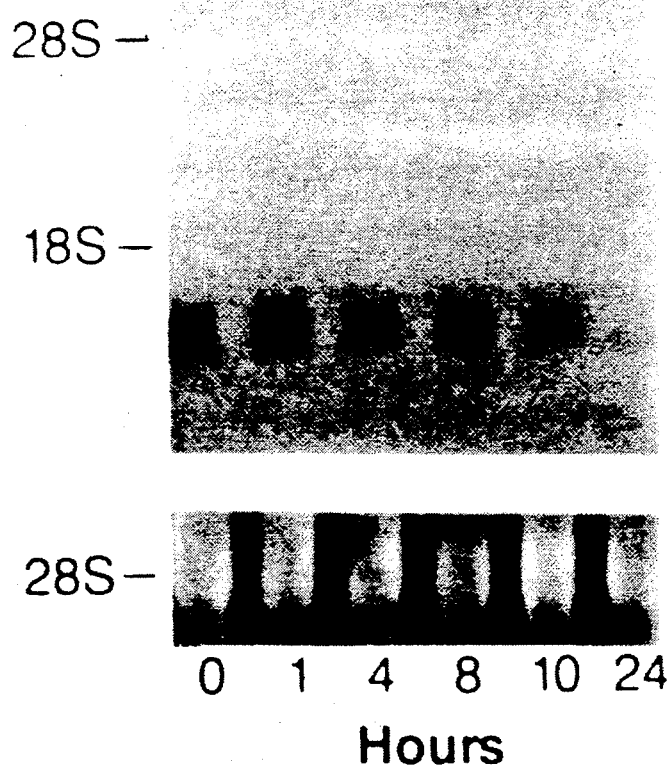

Regulation of Myeloblastin mRNA by Inducers or HL-60 Differentiation and by Serum FIGS. 2A–2D Autoradiograms of RNA blots of myeloblastin mRNA in HL-60 cells treated for various periods of time with: FIG. 2A PMA FIG. 2B 1,25-$(OH)_2D_3$ FIG. 2C RA, and FIG. 2D $Me_2SO$.

FIG. 2E Down-regulation of myeloblastin mRNA by serum starvation.

FIG. 2E(1) Northern blot analysis of myeloblastin mRNA from HL-60 cells maintained in normal tissue culture conditions (10% fetal calf serum) (+), or serum-free conditions for 2 days (−).

FIG. 2E(2) Growth of HL-60 cells under the same conditions as in FIG. 2E(1). Cell numbers are indicated as well as the number of days.

Figure 2B:
Figure 2B:
Figure 2C:
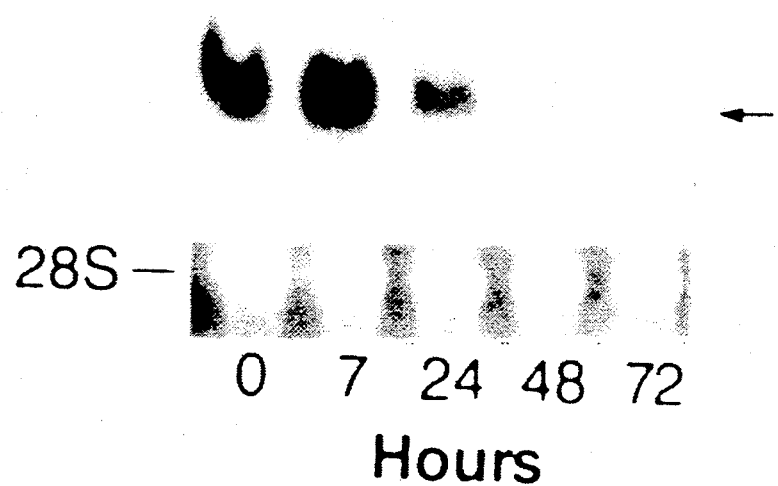
Figure 2D:
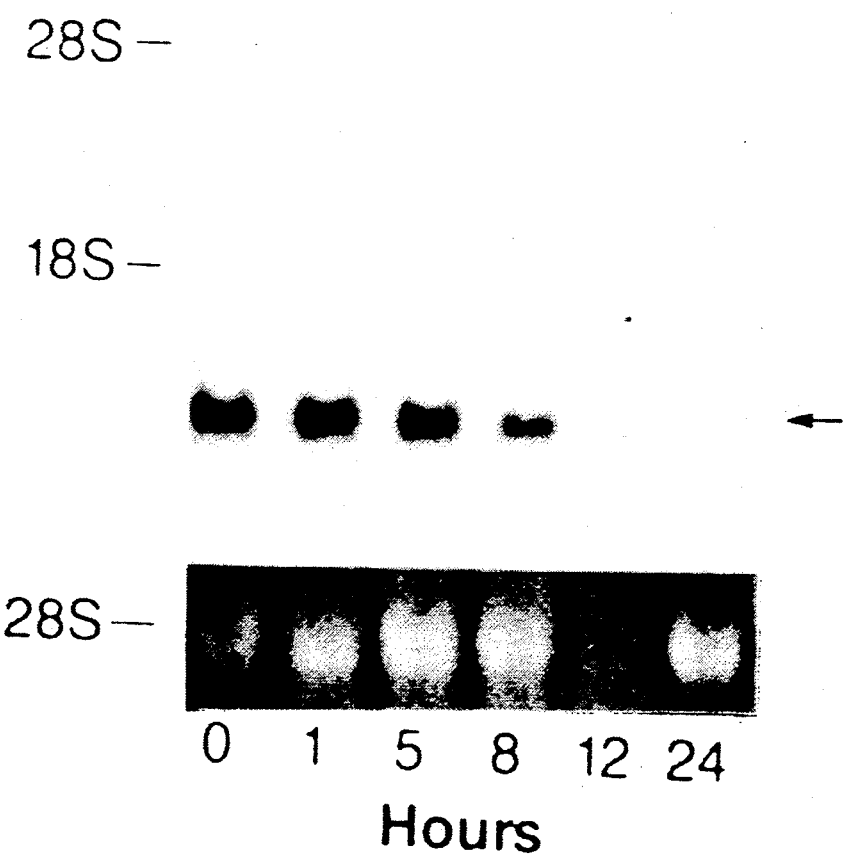
Figure 2F:
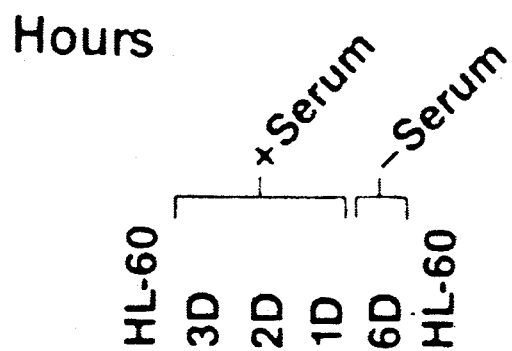

FIG. 2F Up-regulation by reexposure to serum. "−serum" are HL-60 cells cultured in serum-free medium for 6 days; "+serum" are the same cells reexposed to the medium containing 10% fetal bovine serum for 1,2, and 3 days. Control HL-60 cells were in exponential growth. For the RNA blots, the 28S and 18S rRNAs are indicated as markers, and the lower parts are ethidium bromide-stained 28S rRNA from gels prior to transfer. The position of myeloblastin mRNA is indicated by an arrow.

FIG. 3

Identification of Myeloblastin

FIG. 3A SDS-PAGE analysis of anti-myeloblastin immunoprecipitates of [$^3$H]DFP-labeled protein extracts from HL-60 cells. "i" and "ni" indicate immune and nonimmune sera, respectively.

Figure 3B:
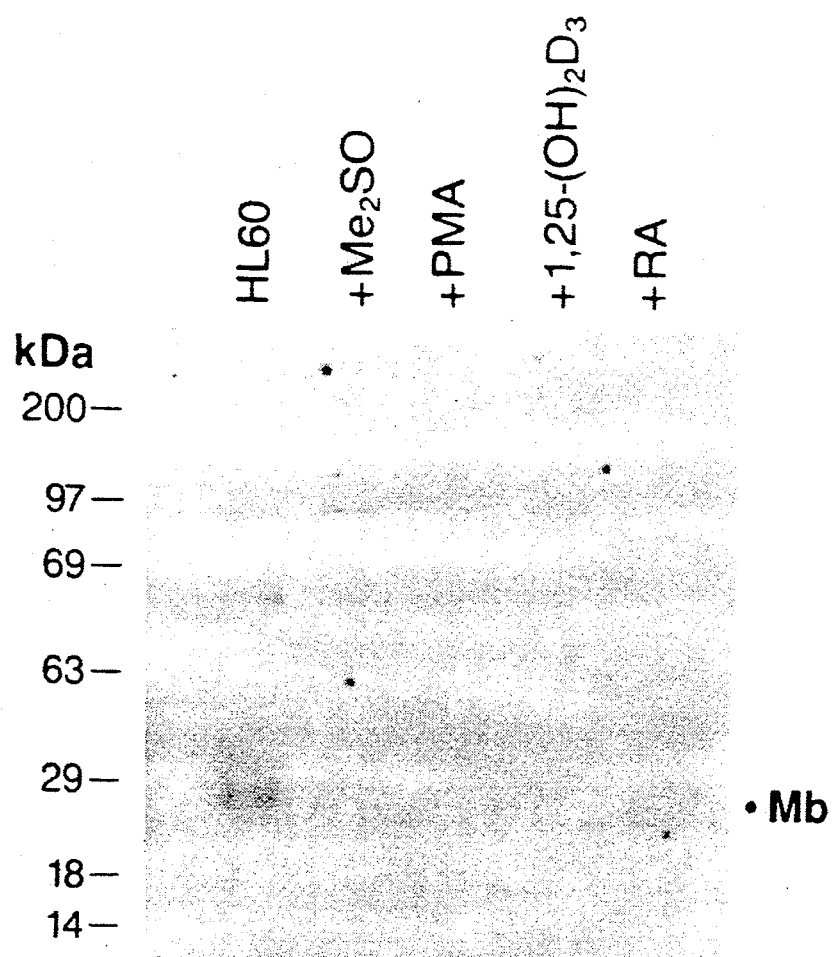

FIG. 3B Immunoblotting of protein extracts from HL-60 cells before and after treatment with different inducers of differentiation. Inducers are as indicated.

Figure 3C:
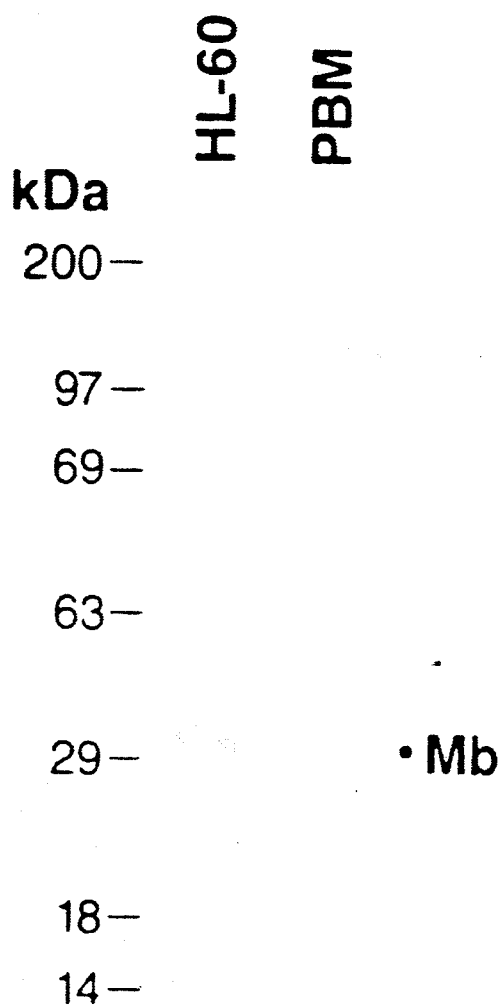

FIG. 3C Immunoblotting of protein extracts from HL-60 and normal human PBMs.

FIG. 3D Fluorography of [$^3$H]DFP-labeled protein extracts from HL-60 cells before (−) and after (+) treatment by PMA. All hybridizations were conducted using an affinity-purified antiserum. Molecular size markers are as indicated. Mb indicates myeloblastin.

FIG. 4

Characteristics of the Antisense-mbn Oligodeoxynucleotide

Figure 4A:
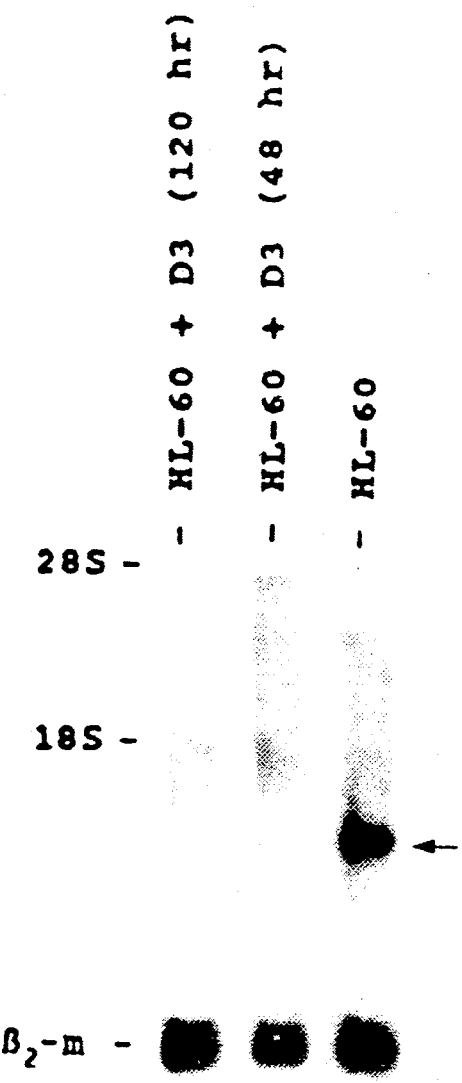

FIG. 4A Hybridization of the antisense-mbn oligodeoxynucleotide to myeloblastin mRNA. HL-60 cells treated with 1,25-$(OH)_2D_3$ for 48 and 120 hr are controls for down-regulation of myeloblastin mRNA. The lower part is the same blot hybridized with a $\beta_2$-microglobulin ($\beta_2$-m) cDNA probe for assessment of quantities of RNA in each lane 28S and 18S ribosomal RNA re indicated as size markers. The arrow indicates the position of myeloblastin mRNA.

Figure 4B:
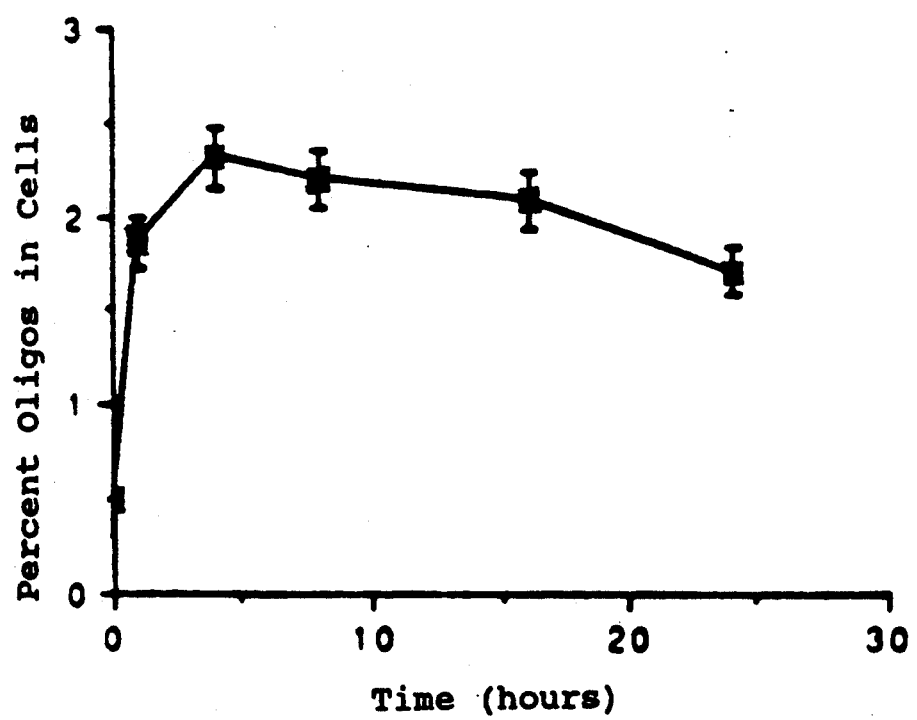

FIG. 4B Uptake of the antisense-mbn oligodeoxynucleotide by HL-60 cells. 5'$^{32}$P-labeled antisense-mbn oligomer was incubated with HL-60 cells for 0, 2, 4, 8, 16, and 24 hr. Squares represent the mean result of three experiments. Bars represent the mean ± standard errors.

Figure 4C:
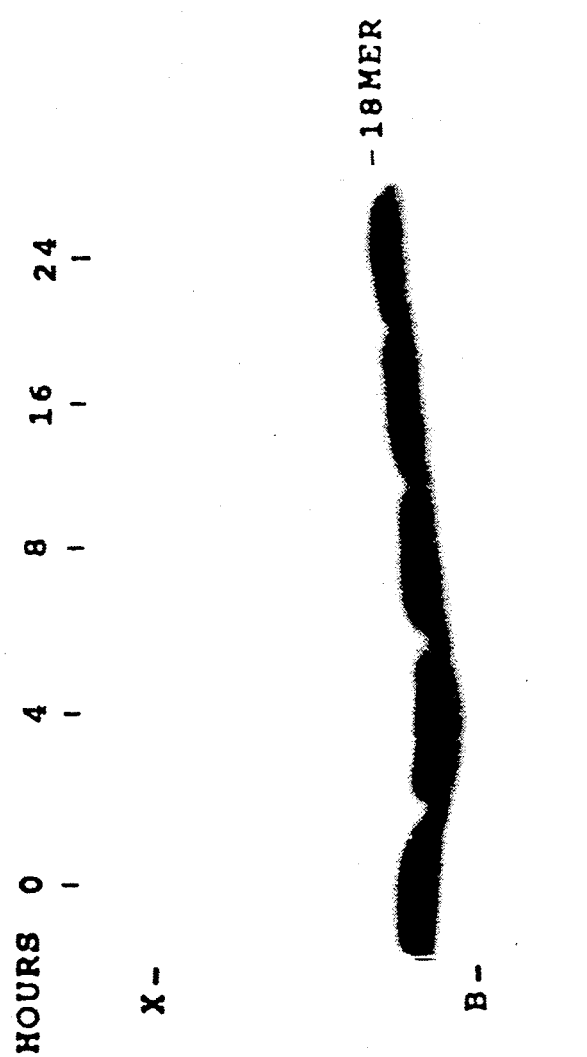

FIG. 4C Stability of the antisense-mbn oligodeoxynucleotide in HL-60 cells. 5'-$^{32}$P-labelled antisense-mbn oligomer was incubated with HL-60 cells for 0, 4, 8, 16, and 24 hr. X and B, mobility of xylene cyanol and bromophenol blue, respectively.

Figure 4D:
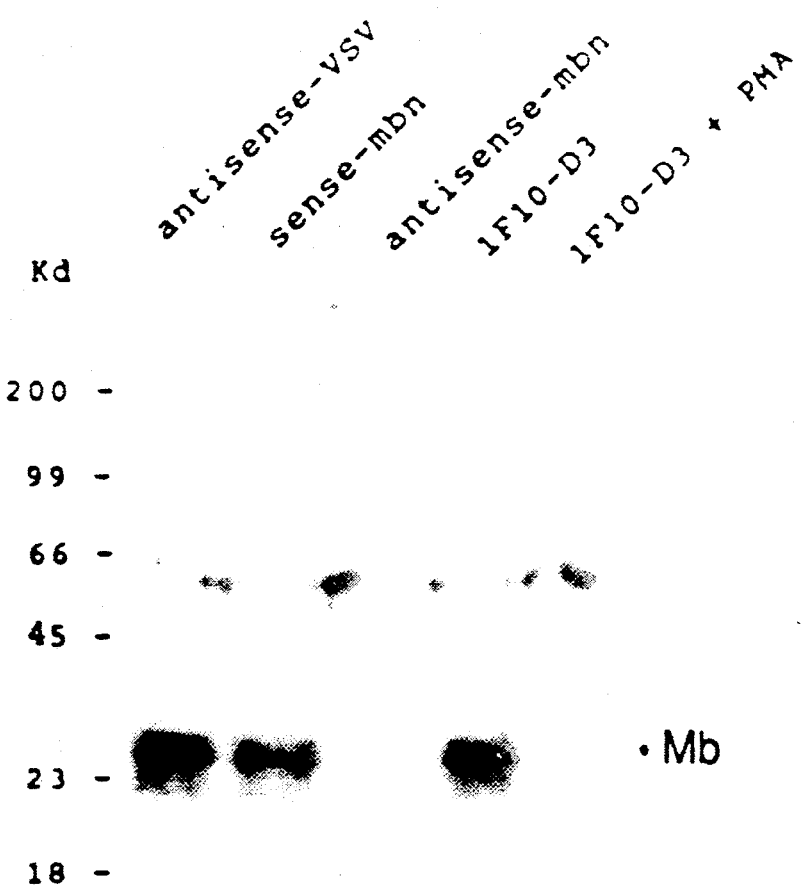

FIG. 4D Inhibition of myeloblastin expression by the antisense-mbn oligodeoxynucleotide. Immunoblot of protein extracts of 1F10-D3 cells untreated and treated with the antisense-mbn, sense-mbn, and antisense-VSV oligomers for 10 days. 1F10-D3 cells treated for 10 days with PMA are a control for down-regulation of myeloblastin. Molecular size markers are as indicated. Mb indicates myeloblastin.

FIG. 5

Morphological Characteristics of 1F10-D3 Cells Untreated and Treated with Different Oligodeoxynucleotides.

Figures 5A, 5B, 5C, 5D, 5E:
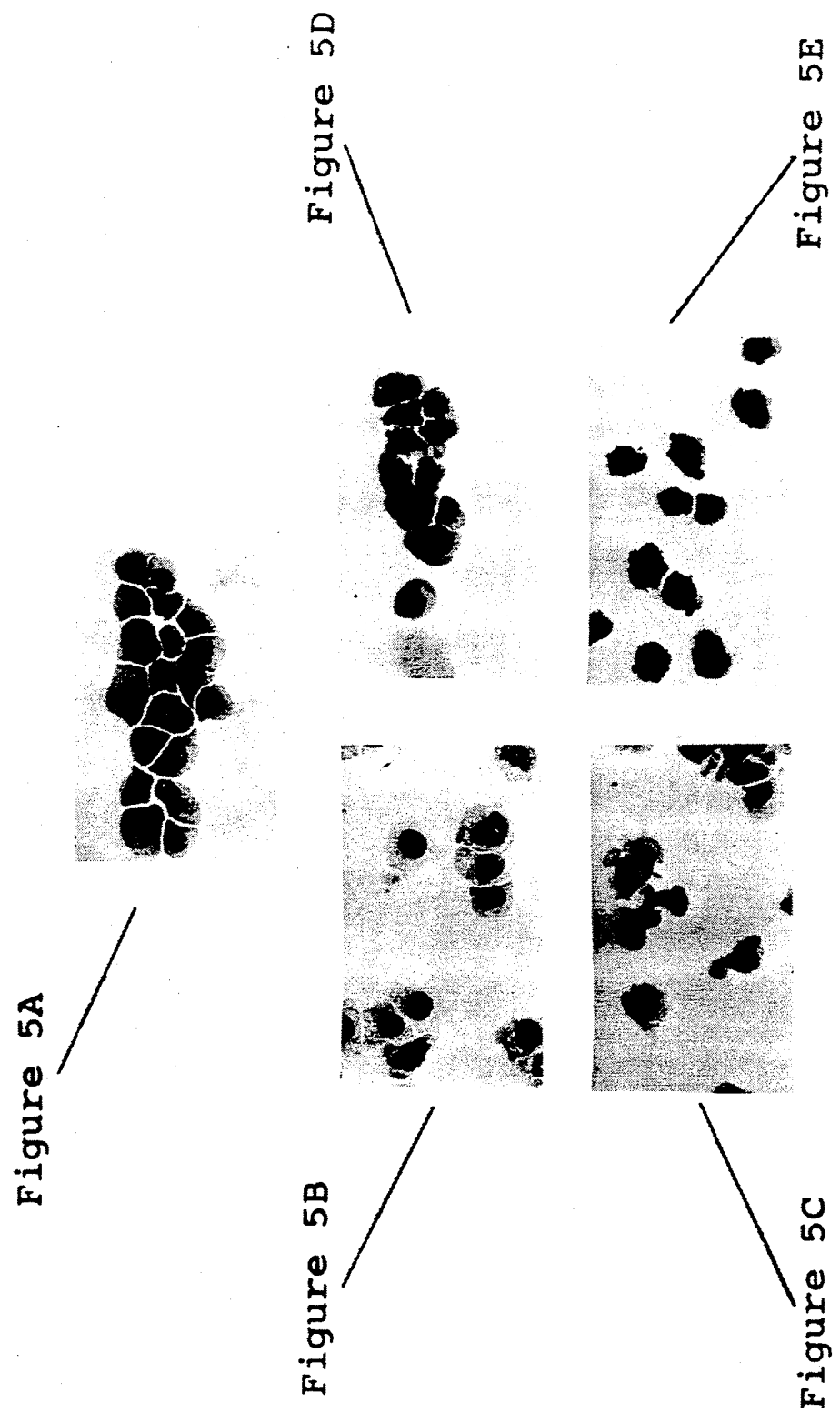

FIG. 5A 1F10-D3 cells.

FIG. 5B 1F10-D3 cells treated for 10 days with the antisense-mbn oligodeoxynucleotide.

FIG. 5C 1F10-D3 cells treated for 12 days with the antisense-mbn oligodeoxynucleotide.

FIG. 5D 1F10-D3 cells treated with sense-mbn oligodeoxynucleotide for 10 days.

FIG. 5E 1F10-D3 cells treated for 10 days with the antisense-VSV oligodeoxynucleotide.

FIG. 6

Effects of Antisense-mbn Oligodeoxynucleotide on Expression of CR3 and Regulation of Cell Growth.

Figure 6A:
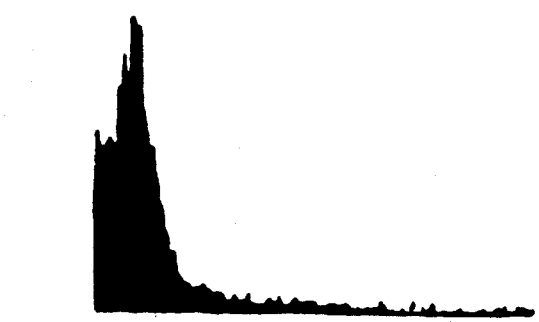
Figure 6A:
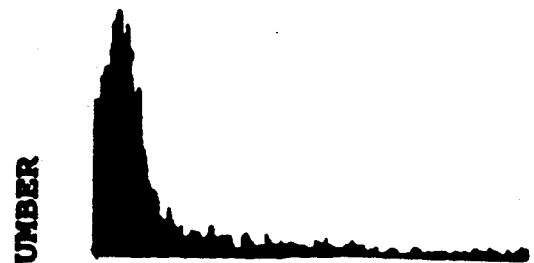
Figure 6A:
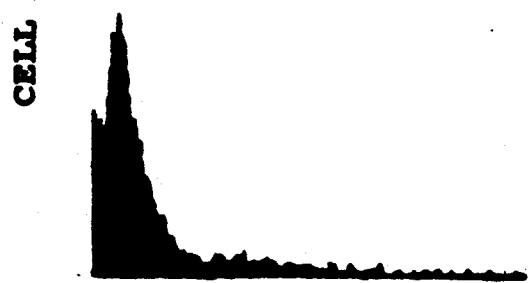
Figure 6A:
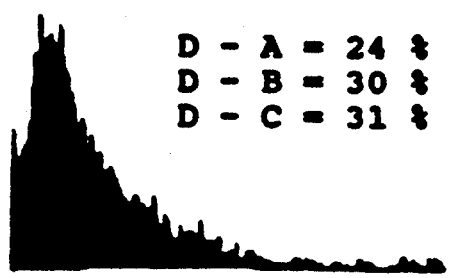

FIG. 6A Fluorescence labeling of CR3 with the OKM1 monoclonal antibody and fluorocytometry analysis of 1F10-D3 cells untreated and treated for 10 days with different oligodeoxynucleotides.

FIG. 6A(1) 1F10-D3 cells.

FIG. 6A(2) 1F10-D3 cells treated with sense-mbn oligodeoxynucleotide.

FIG. 6A(3) 1F10-D3 cells treated with antisense-VSV oligomer.

FIG. 6A(4) 1F10-D3 cells treated with antisence-mbn oligodeoxynucleotide. Percentages of positive cells in FIG. 6A(4) as compared with FIG. 6A(1), FIG. 6A(2), FIG. 6A(3) indicated in FIG. 6A(4).

Figure 6B:
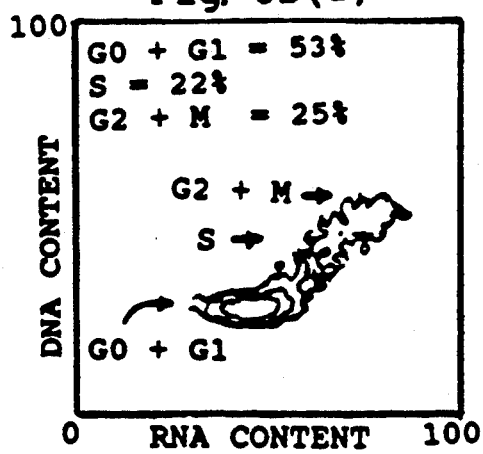
Figure 6B:
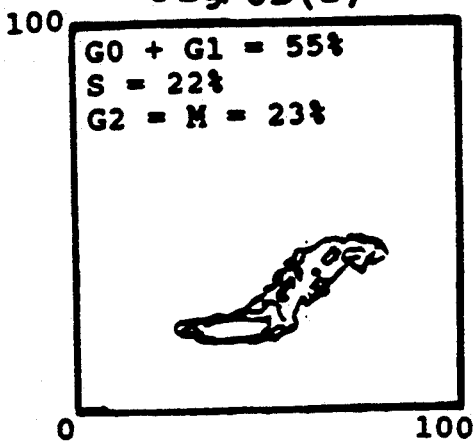
Figure 6B:
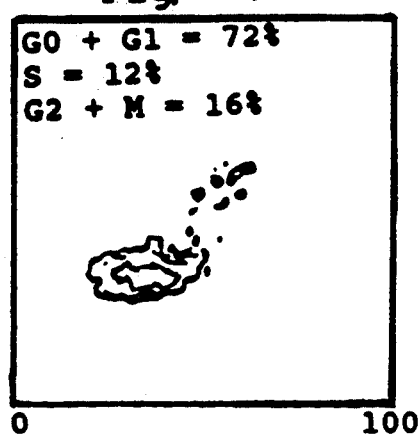
Figure 6B:
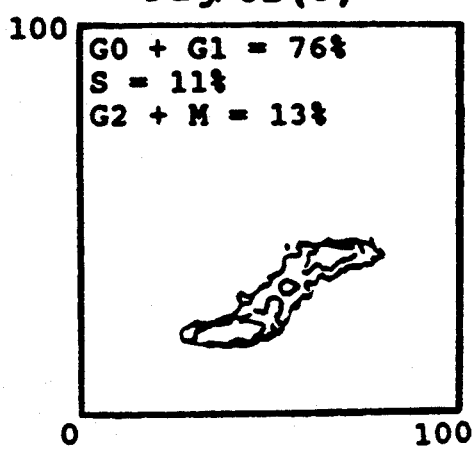
Figure 6B:
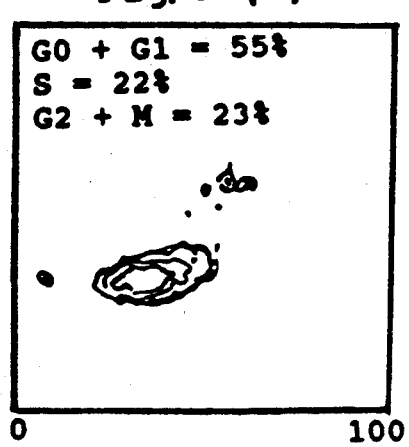

FIG. 6B Bivariate (DNA/RNA) distribution of 1F10-D3 cells untreated and treated with different oligodeoxynucleotides.

FIG. 6B(1) 1F10-D3 cells.

FIG. 6B(2) 1F10-D3 cells treated with the sense-mbn oligodeoxynucleotide.

FIG. 6B(3) 1F10-D3 cells treated with the antisense-VSV oligodoexynucleotide.

FIG. 6B(4) 1F10-D3 cells treated with antisense-mbn oligodeoxynucleotide.

FIG. 6B(5) 1F10-D3 cells treated with PMA (107 mM).

y and x axes on each map represent DNA and RNA contents, respectively. The data are shown as isometric contour maps. Sequential contours represent increasing isometric levels equivalent to 2, 4, 8, 16, and 32 cells, respectively; $10^4$ cells were counted per sample. The data on the cell cycle distributions shown in the insets were obtained by deconvolution of the DNA frequency histograms following cell staining with the DNA-specific fluorochrome 4'6-diamidino-2-phenylindole (DAPI) as described (Darzynkiewicz, et al., 1984).

DETAILED DESCRIPTION OF THE INVENTION

This invention provides an isolated nucleic acid molecule encoding a myeloblastin, such as an isolated DNA, cDNA, or RNA molecule, and in particular such isolated nucleic acid molecules encoding human myeloblastin.

This invention also provides a cDNA molecule having a coding sequence complementary or identical to a sequence included within the coding sequence shown in FIG. 1D.

This invention further provides an oligonucleotide at least 10 nucleotides in length complementary or identical to a nucleic acid molecule encoding myeloblastin, such as an oligonucleotide having a sequence complementary or identical to a sequence included within the coding sequence shown in FIG. 1D. Specific examples are a nucleic acid probe comprising DNA or RNA labelled with a detectable marker, in particular a radiolabelled molecule, a fluorescent molecule, an enzyme, or a ligand, and an antisense oligonucleotide having a sequence complementary to myeloblastin mRNA. A further example of an antisense oligonucleotide is an oligonucleotide having the sequence 5'-d(CTGGGGTATGTCCCGCAG)-3'.

This invention provides a purified polypeptide having substantially the same amino acid sequence as the amino acid sequence shown in FIG. 1D and having the biological activity of human myeloblastin. An example of such a purified polypeptide is purified naturally occurring human myeloblastin.

This invention provides an antibody directed to an epitope present on human myeloblastin, such as an antibody directed to an epitope having an amino acid sequence substantially the same as any part of the amino acid sequence shown in FIG. 1D, in particular an antibody directed against a 16-amino acid long peptide having the sequence Val Phe Leu Asn Asn Tyr Asp Ala Glu Asn Lys Leu Asn Asp Ile Leu. Examples of antibodies are monoclonal antibodies, which are prepared by methods well known in the art; namely by injecting human myeloblastin into an animal, obtaining from the animal a B-lymphocyte producing an antibody against an epitope on human myeloblastin, and fusing the B-lymphocyte with a myeloma cell to create a hybridoma producing the antibody.

This invention provides a pharmaceutical composition comprising an amount of an antisense oligonucleotide complementary to human myeloblastin mRNA, for example an oligonucleotide having the sequence 5'd(CTGGGGTATGTCCCGCAG)3', effective to inhibit proliferation and induce differentiation of leukemia cells, and a pharmaceutically acceptable carrier, such as distilled water, saline, and other fluid or solid carriers. In one embodiment, the pharmaceutical composition further comprises an amount of a stabilizer effective to bind to the oligonucleotides. In another embodiment, the pharmaceutical composition further comprises a tracing substance.

This invention provides a molecule that inhibits the protease activity of myeloblastin and a factor that suppresses the transcription of myeloblastin by binding to the repressor region of the myeloblastin gene so as to prevent the transcription of myeloblastin mRNA. Both the inhibitor and the factor impede myeloblastin activity in a cell such as a leukemia cell, which has the effect of reversing certain abnormalities in the leukemia cell, namely proliferation and inability to differentiate. The inhibitor is isolated by in vitro binding assays with purified myeloblastin using methods well known in the art. In another method, natural or synthetic molecules are contacted with a myeloblastin substrate and myeloblastin. A molecule that prevents myeloblastin from cleaving its substrate is thereby identified as an inhibitor of myeloblastin. The factor is isolated by detecting protein bound to the repressor region of the myeloblastin gene in cells whose expression of myeloblastin has been down-regulated. The repressor region is isolated and sequenced, and an oligomer having the repressor sequence is produced and used as a detectable probe for the factor. A cell extract from cells known to produce myeloblastin is contacted with such an oligomer. When an oligomer that has been contacted with cell extract is run on a gel, it will migrate more slowly than the same oligomer not contacted with cell extract. The factor bound to the oligomer is thus identified by this gel shift. The repressor region of the myeloblastin gene is within the promotor region, and is therefore found by locating the gene's promoter region. The promoter is 5' to the cap site of the gene. The cap site sequence is determined by primer extension of myeloblastin mRNA. An oligonucleotide probe having a corresponding sequence is synthesized and used to probe for the cap site in the genomic DNA. DNA around the cap site is isolated and cut at different sites to create a set of overlapping deletion mutants which are cloned into vectors comprising a reporter gene such as CAT. These deletion mutants are expressed in host cells. The clone that causes expression of CAT contains the promoter, which is needed to promote expression of CAT. That clone is then sequenced to obtain the promoter and repressor sequences.

This invention provides a method for identifying a leukemia cell which expresses myeloblastin comprising contacting the cell with a nucleic acid probe for myeloblastin, such as a DNA or RNA probe labelled with a detectable marker, under conditions well known in the art which permit the probe to hybridize to mRNA encoding myeloblastin if any such is present, and detecting expression by detecting by methods well known in the art any hybridization which occurs. Quantification of the amount of mRNA detected is also performed by methods well known in the art, such as gel electrophoresis against markers, counting in a scintillation counter, or use of columns or ELISA or enzyme assays depending on the type of detectable label the probe is labelled with. An example of a cell is a human leukemia cell. Absence of down-regulation of myeloblastin expression indicates abnormality. Production of myeloblastin distinguishes lymphoblastic undifferentiated leukemia cells from myeloid undifferentiated leukemia cells. The latter cells produce myeloblastin and the former cells do not. It is otherwise difficult to determine cell types in undifferentiated leukemia. In addition, the level of expression of myeloblastin in a given type of leukemia cell, i.e., myeloblastic, acute promyelocytic, myelomonocytic, or monocytic, correlates to the rate of development of the leukemic cell and thus provides information relevant to prognosis, for example rapidity of onset and possible resistance to treatment.

This invention provides a method for inhibiting proliferation and inducing differentiation of a leukemia cell which comprises contacting the leukemia cell with an antisense oligonucleotide complementary to human myeloblastin mRNA, such as an oligonucleotide having the sequence 5'd(CTGGGGTATGTCCCGCAG)3', so as to allow hybridization of the oligonucleotide to myeloblastin mRNA in the cell, thereby preventing translation of myeloblastin mRNA and production of myeloblastin, resulting in inhibition of proliferation and induced differentiation of the leukemia cell. An example of a cell is a human leukemia cell. The antisense oligonucleotide functions by binding to mRNA encoding myeloblastin in a target leukemia cell and thereby preventing the translation of myeloblastin. Reducing the level of myeloblastin in the target leukemia cell inhibits its proliferation and leads to its differentiation, i.e., the reduction of myeloblastin levels in a leukemia cell causes the cell to resume normal behavior by reversing abnormalities in the affected cell.

This invention provides a method of treating a subject with leukemia comprising contacting the affected cells with an amount of an antisense oligonucleotide complementary to human myeloblastin mRNA effective to inhibit their proliferation and induce their differentiation. An example of an antisense oligonucleotide is an oligonucleotide having the sequence 5'd(CTGGGGTATGTCCCGCAG)3'.

This invention provides a method of treating a subject with leukemia which comprises administering to the subject an amount of a pharmaceutical composition effective to inhibit proliferation and induce differentiation of leukemia cells. The pharmaceutical composition comprises an antisense oligonucleotide, a pharmaceutically acceptable carrier, a stabilizing substance, and a tracing substance. The antisense oligonucleotide is complementary to human myeloblastin mRNA. A specific example of an oligonucleotide is an oligonucleotide having the sequence 5'd(CTGGGGTATGTCCCGCAG)3'. The stabilizer increases the half-life of the oligonucleotides. The pharmaceutical composition is injected into the subject and reaches its target bone marrow through the circulation. The oligonucleotides penetrate the target cells and inhibit myeloblastin transcription in target leukemia cells as described supra. The antisense oligonucleotide is highly specific for myeloblastin mRNA and therefore does not bind to other known mRNA. Its only possible effect on normal cells would be to accelerate their maturation process.

This invention also provides a method of determining whether a molecule is effective as an inhibitor of myeloblastin activity in leukemia cells which comprises propagating leukemia cells in a mouse with severe combined immunodeficiency (SCID mouse), injecting the molecule into the mouse, and determining whether the molecule is effective as an inhibitor of myeloblastin activity by determining whether the mouse is cured of leukemia symptoms. Examples of molecules are proteins and nucleic acid oligomers.

This invention also provides a method of treating a subject with leukemia which comprises propagating the subject's bone marrow cells in a mouse with severe combined immunodeficiency and determining whether a molecule will inhibit myeloblastin activity in that subject by injecting the molecule into the mouse, determining whether the molecule is effective as an inhibitor of myeloblastin activity in that subject by determining whether the mouse is cured of leukemia symptoms and treating the subject with the molecule if the molecule is effective as a myeloblastin inhibitor. Examples of molecules are proteins and nucleic acid oligomers. This approach is especially useful in cases where a subject is resistant to chemotherapy. A treatment specifically effective for a particular subject's cells can be designed using this method. A SCID mouse lacks immune defenses, therefore foreign cells such as human leukemic bone marrow cells are able to multiply in such a mouse until they constitute a majority of the bone marrow population, and cause the mouse to exhibit symptoms of leukemia. A system is thereby provided for in vivo work with human bone marrow cells. Curing such a mouse of leukemia symptoms by use of a molecule indicates that this molecule is effective to reverse the abnormalities in the human leukemia cells with which the mouse has been populated.

This invention provides a method of preparing purified myeloblastin which comprises homogenizing human cells that express myeloblastin, isolating serine proteases from the resulting homogenate using an affinity column comprising a serine protease inhibitor which binds to serine proteases in the homogenate, for example a benzamidine-Sepharose 6B column (Pharmacia, Piscataway, N.J.), running the resulting serine proteases over an FPLC column and isolating the resulting fractions, purifying the resulting fractions by contacting them with an ion exchange column, and determining which fraction contains myeloblastin by contacting each fraction with an antibody directed to an epitope on myeloblastin and determining whether the myeloblastin in the fraction binds to the antibody. An example of a human cell is a human leukemia cell, such as an HL-60 cell or a cell of the 1F10 cell system. The antibodies can be bound to a solid support or be bound to detectable markers.

This invention further provides a method of preparing purified human myeloblastin which comprises cloning an isolated nucleic acid molecule encoding myeloblastin, such as a DNA or cDNA molecule, into an expression vector comprising a promoter and a fusion gene, transfecting a suitable host cell with the resulting expression vector and propagating the host in a suitable culture medium so that a myeloblastin fusion protein consisting of myeloblastin and the fusion gene product are produced by the host cell, and isolating myeloblastin from the resulting culture medium by contacting the culture medium with an affinity column to which the fusion gene product binds to isolate the myeloblastin fusion protein and cleaving off the fusion gene product to produce myeloblastin. A specific fusion gene is the $\beta$-galactosidase gene, producing $\beta$-galactosidase which can be isolated on a column comprising antibodies directed to $\beta$-galactosidase bound to a solid support.

The invention will be better understood by reference to the Experimental Details which follow, but those skilled in the art will readily appreciate that the specific experiments detailed are only illustrative of the invention as described more fully in the claims which follow hereafter.

Experimental Details

Cells from the human leukemia cell line HL-60 undergo terminal differentiation when exposed to inducing agents. Differentiation of these cells is always accompanied by withdrawal from the cell cycle. Here we describe the isolation of a cDNA encoding a novel serine protease that is present in HL-60 cells and is down regulated during induced differentiation of these cells. We have named this protease myeloblastin. Down-regulation of myeloblastin mRNA occurs with both monocytic and granulocytic inducers. Myeloblastin mRNA is undetectable in fully differentiated HL-60 cells as well as in human peripheral blood monocytes. We found that regulation of myeloblastin mRNA in HL-60 cells is serum dependent. Inhibition of myeloblastin expression by an antisense oligodeoxynucleotide inhibits proliferation and induces differentiation of promyelocyte-like leukemia cells.

Materials and Methods

Cells and Culture Conditions: Cells were grown in RPMI 1640 medium with 10% fetal bovine serum and 2 mM L-glutamine. Adherent cells were scraped before RNA or protein preparations. PMA (Sigma Chemical Co., St. Louis, Mo.) in $Me_2SO$ was used at a final concentration of 107 nM. The final concentration of $Me_2SO$ was 0.002% and had no effect on differentiation. 1,25-$(OH)_2D_3$ was dissolved in 95% (v/v) ethanol and used at a final concentration of 0.6 $\mu$M. Retinoic acid dissolved in 95% (v/v) ethanol was used at a final concentration of 0.1 $\mu$M. $Me_2SO$ was used at a final concentration of 1.25%. Human PBMs (New York Blood Program) were obtained from normal volunteers. After Ficoll-Paque gradient centrifugation (Pharmacia, Piscataway, N.J.), cells were washed and allowed to adhere for 4 hours to tissue culture flasks. U937 is a human monocytoid cell line, KG-1 is a human myeloblastic cell line, and K562 cells are early myeloid blasts and/or erythroblasts. For morphological assessment of differentiation, cells were washed three times in phosphate-buffered saline (PBS), cytocentrifuged (1250 rpm, 5 min),and stained with Wright/Giemsa.

Subtraction cDNA Hybridization and Blot Hybridization: cDNA was synthesized in the presence of actinomycin D and subtracted as described (Solomon, et al., 1988). Our mRNA-cDNA hybridization conditions achieved a $C_o t$ value of 3000 for the RNA. The cDNA subtraction resulted in the removal of 98% of its mass after hydroxyapatite chromatography. The second cDNA strand was synthesized with reverse transcriptase (Life Sciences, St. Petersburg, Fla.) by dC-tailing of the first strand (Rowekamp and Firtel, 1980) followed by priming with oligo$(dG)_{12-18}$ (Collaborative Research, Waltham, Mass.) (Rowekamp and Firtel, 1980; Land, et al., 1981). The double-stranded cDNA was digested with S1 nuclease (Boehringer Mannheim), then 3' dC-tailed and annealed with a Pst1-cut 3'dG-tailed pUC9 vector previously purified by using an oligo(dC)-cellulose column to remove untailed molecules (Rowekamp and Firtel, 1980; Land, et al., 1981). Fifteen microliters of annealing mixture (5 ng vector) was used for transforming 100 $\mu$l of competent RR1 bacteria (Bethesda Research Laboratories) according to a standard procedure (Hanahan, 1983). The transformation efficiency was $1.4 \times 10^5$ transformants per $\mu$g of insert DNA. The resulting 5300 ampicillin-resistant bacteria clones were subjected to a differential screening procedure using both subtrated (1F10-$D_3$ cDNA minus 1F10-PMA mRNA) and unsubtracted (1F10-PMA cDNA) cDNA probes. DNA from each selected clone was used as a nick-translated probe to hybridize with RNA blots of poly(A)+RNA from 1F10 as well as 1F10-PMA and 1F10-$D_3$ cells.

RNA Isolation and RNA Blot Analysis: Cytoplasmic RNA was extracted from cells as described (Mushinski, et al., 1980) and prepared according to Chirgwin, et al. (1979). Poly (A)+ mRNA was isolated on an oligo(dT)-cellulose column (Collaborative Research). Total RNA was isolated as described above (Chirgwin, et al. 1979). For RNA blots, RNA preparations were denatured and processed as described (Schleicher & Schuell). All RNA blots contained 10 $\mu$g of RNA per lane. The filters were hybridized to $2 \times 10^6$ cpm ml of the myeloblastin nick-translated probe (radiolabeled to a specific activity of $7.5 \times 10^7$ cpm/$\mu$g) and then washed (Hofer and Darnell, 1981). When indicated, a $\beta_2$-microglobulin nick-translated cDNA probe (Suggs, et al., 1981) was used for assessment of RNA quantities in each lane.

Sequence Determination of Cloned Myeloblastin cDNA and Computer Analysis: The myeloblastin cDNA sequence consists of four overlapping cDNAs: Sp-120.1, SP-120.13, SP-120.8.2, and SP-120.28.1. These cDNA clones were subcloned into M13 and sequenced by the dideoxy chain termination method (Sanger, et al., 1977). The coding strand was determined by RNA blot hybridization by using single-stranded probes prepared from M13 subclones corresponding to each strand. The dfastp program (Lipman and Pearson, 1985) was used to search for amino acid similarities.

Antibodies: The myeloblastin-derived peptide was synthesized on an automated Biosearch peptide synthesizer according to the deduced amino acid sequence. The quality of the peptide was verified by high performance liquid chromatography and amino acid analysis. The peptide was coupled to keyhole limpet hemocyanin (Behring Diagnostics) through a cysteine residue added to the carboxy-terminal amino acid of the peptide. m-Maleidobenzoyl-N-hydroxysuccinimide (Pierce Chemical Co.) was used as a coupling agent (Lerner, et al., 1981). Coupling efficiency was verified as described (Bolton and Hunter, 1973). The coupled peptide was injected near the lymph nodes into three rabbits at BAbCO (Berkeley, Calif.). After the third injection the rabbits were bled and their sera tested for reaction with the myeloblastin peptide by ELISA (Engvall, 1980). Antiserum from a single bleed of one rabbit was used throughout this study. The antiserum was affinity purified on a column of myeloblastin peptide immobilized on activated CH-Sepharose 4B (Pharmacia, Piscataway, N.J.).

Immunoblotting: Immunoblots were prepared as described (Towbin, et al., 1979). Cell extracts were prepared in the presence of 1% boiling SDS and maintained for another 5 min in a boiling water bath (Albert, et al., 1986). Proteins were separated on a 12.5% polyacrylamide gel (Laemmli, 1970). Protein transfer to nitrocellulose membrane (Scheicher & Schuell) was performed at a constant current of 150 mA for 12 hr. Hybridization was performed with an affinity-purified anti-peptide antibody followed by 0.1 $\mu$Ci/ml of $^{125}$I-labeled protein A (New England Nuclear).

DFP Labelling: DFP labeling was performed as described (Pasternack and Eisen, 1985). In brief, cells were washed twice in fresh medium and in PBS, then resuspended in 0.5% NP-40-PBS and incubated on ice for 30 min while vortexed several times. [1.3-$^3$H]DFP (4.4 Ci/mmol, New England Nuclear) was added to a 300 $\mu$l extract of 3 to 6×10$^6$ cells to a final concentration of 10$^{-5}$ M. After a 30 min incubation at 37° C., the reaction was stopped by adding Tris-HCl(pH 8.1) to a final concentration 15 mM and SDS to 0.1%. Samples were centrifuged at 8000×g for 15 min. The supernatants were concentrated to a 100 $\mu$l volume, and the labeled protein was recovered by cold acetone precipitation. The pellet was dissolved in sample buffer with 5% mercaptoethanol and analyzed on a 12.5% SDS-polyacrylamide gel. Gels were exposed to Enlightning (New England Nuclear), dried, and exposed at −70° C. using XAR-5X-ray film (Eastman Kodak). For imunoprecipitation of the DFP-labeled material, samples were denatured by boiling in 1% SDS, neutralized in 6% NP-40, and treated with 40 $\mu$l of the antipeptide antiserum or nonimmune serum. Immune complexes were collected with 200 $\mu$l of a 10% suspension of 1 gGsorb (The Enzyme Center, Malden, Mass.). Precipitates were analyzed on a 12.5% polyacrylamide gel (Laemmli, 1970). Radiolabeled protein bands were visualized by fluorography (Bonner and Laskey, 1974) with Enlightning (New England Nuclear).

Oligodeoxynucletide Synthesis, Cellular Uptake, and Stability: Unmodified deoxynucleotides were synthesized on an automated solid-phase synthetizer by using standard phosphoraminide chemistry. Deoxynucleotides were purified by polyacrylamide gel electrophoresis. All oligomers were lyophilized and suspended in H$_2$O. The synthesis was carried out at the Columbia University facility. Oligonucleotide uptake and intracellular stability were assayed as described (Wickstrom et al., 1988). In brief, oligonucleotides were 5'-labelled with (gamma-$^{32}$P]ATP (3000 Ci/mmol: 1 Cl=37 GBq by use of bacteriophage T4 polynucleotide kinase and then purified by denaturating gel electophoresis. For each time point, 5×10$^4$ cpm of labeled oligonucleotides was added to 4×10$^6$ cells in normal tissue culture medium. Cells were then incubated at 37° C. for 1, 4, 8, or 24 hr, then washed, and the percent uptake was determined as described (Wickstrom, et al., 1988). For assessment of hybridization arrest of translation, a quantitative immunoblot was prepared with protein extracts from untreated 1F10-D3 cells as well as 1F10-D3 cells treated with antisense-mbn oligodeoxynucleotide, sense-mbn, antisense-VSV, and PMA. this blot was hybridized with anti-myeloblastin antibodies made against a synthetic peptide as described above.

Assays for detection of Differentiation Markers: OKM1 is a monoclonal anti-human antibody directed against an epitope on CR3 (Fleit, et al., 1984; Wright, et al., 1983). CR3 is induced in differentiated HL-60 cells (American Type Culture Collection, Rockville, Md.; Fleit, et al., 1984). The CR3 determinant was detected by binding a fluoresceinated OKM1 monoclonal mouse anti-human antibody (OKM1-FITC; Cappel Laboratories, Cochranville, Pa.); cells were analyzed on a fluorescence-activated cell sorter, with 10$^4$ cells being counted in each experiment. Acid $\alpha$-acetate esterases (Mueller, et al., 1975) are characteristic of monocytes.

Cell Cycle Analysis: The DNA content of individual cells was measured by flow cytometry (Darzynkiewicz, et al., 1984). Experiments were repeated twice.

Results

Isolation of a Myeloblastin cDNA Clone and Cell Distribution of Myeloblastin mRNA: cDNA subtraction was applied to the 1F10 system as previously described (Solomon, et al., 1988). This subtraction strategy, together with differential screening and RNA blot analysis, has been used in the 1F10 system to permit identification of genes that are either induced by 1,25-(OH)$_2$-D$_3$ but not by PMA or are down-regulated by PMA and not by 1,25-(OH)$_2$D$_3$. To verify the differential screening, RNA blot analysis of poly(A)+RNAs from 1F10 cells under different culture conditions was performed. FIG. 1A shows that the 1F10-D3 cells expressed a transcript of approximately 1.3 kb hybridizing strongly with the radiolabeled myeloblastin cDNA probe. Expression of myeloblastin mRNA did not depend on the continued presence of 1,25-(OH)$_2$-D$_3$; this mRNA was already expressed in both 1F10 and HL-60 cells. As predicted from the cloning strategy, myeloblastin mRNA was barely detectable in 1F10-PMA cells and its down-regulation in these cells was dependent on the continued presence of PMA. Myeloblastin mRNA was expressed in U937, a human monocytoid cell line (for review, see Koeffler, 1983) and was down-regulated after treatment with PMA (FIG. 2). Myeloblastin mRNA was not expressed in normal human peripheral blood monocytes (PBMs) (FIG. 3).

In contrast to myeloblastin mRNA expression in 1F10 and HL-60 cells, in the less mature human leukemia cell lines, KG-1 and K562, myeloblastin mRNA was not expressed (for review, see Koeffler, 1983) (FIG. 1B). These results suggest that myeloblastin mRNA is expressed in immature cells from the myelomonocytic lineage only at a discrete stage in differentiation. To further investigate this possibility, we are currently assessing the expression of myeloblastin mRNA in primary human leukemia cells.

Myeloblastin is a novel serine protease. The myeloblastin cDNA sequence consists of four overlapping cDNAs: SP-120.1, SP-120.13, SP-120.8.2, and SP-120.28.1. SP-28.1, the longest cDNA, is a 794 bp insert. The longest open reading frame represents 215 amino acids from the beginning of the coding sequence to the stop codon TGA at position 645. As shown in FIG. 1D, the putative initiation codon is surrounded by a ribosomal binding site consensus sequence as underlined (CCCTACATGGCC), which is similar to one previously described (Kozak, 1984). Fifty base pairs of the sequence upstream of position −66 has been determined by oligonucleotide-primed RNA sequencing (Geliebter, et al., 1986), and a unique cap site was identified (data not shown).

Using the programs FASTN and dfastp (Lipman and Pearson, 1985), we searched the National Biomedical Research Foundation library for nucleic acid and protein sequences that might be homologous to myeloblastin. The deduced amino acid sequence of myeloblastin reveals the structural features of a serine protease (FIG. 1D) and shares homology with other serine proteases. Three residues, His-30, Asp-77, and Ser-162, corresponding to the catalytic triad of serine proteases (Hartley, 1970) are found at positions homologous to those of other serine proteases. The primary binding site (Gly-Asp-Ser-Gly-Gly-Pro) at residues 160 to 165 is totally conserved. Human neutrophil elastase (HuNE) has been recently sequenced (Takahashi, et al., 1988); it shows the highest amino acid identity (55%) to the deduced amino acid sequence of myeloblastin (FIG. 1E). Eight cysteine residues occur at identical positions in myeloblastin and in HuNE; in the latter they form internal disulfide bonds as established by X-ray crystallography (Bode, et al., 1986). In myeloblastin, we expect these four conserved disulfide bonds to involve Cys-15-Cys-31, Cys-111-Cys-168, Cys-141-Cys-147, and Cys-158-Cys-183. The fourth disulfide bond is conserved in pancreatic elastase as well as in plasmin, trypsin, chymotrypsin, and HuNE, but not in thrombin and coagulation factor X (Hartley, 1970). Myeloblastin exhibits two potential N-linked glycosylation sites at positions Asn-88 and Asn-133, the first one being identical in both myeloblastin and HuNE.

Myeloblastin mRNA is regulated by several inducers of HL-60 differentiation and by serum. In HL-60 cells, myeloblastin mRNA progressively disappeared after treatment with either PMA or 1,25-$(OH)_2D_3$ (FIGS. 2A and 2B). Inducers of granulocytic differentiation such as RA and $Me_2SO$ also abolished steady-state myeloblastin mRNA levels (FIGS. 2C and 2D). Myeloblastin mRNA disappeared at approximately 10 hours with PMA and $Me_2SO$ and at 48 hours with RA and 1,25-$(OH)_2D_3$ (FIGS. 2A, 2B, 2C, and 2D).

Since growth arrest is always associated with HL-60 cell differentiation, serum starvation has been used to determine whether regulation of myeloblastin mRNA is linked to growth inhibition of these cells. HL-60 cell growth was arrested by culturing cells for 48 hours in the absence of fetal bovine serum; under this condition myeloblastin mRNA was down-regulated (FIG. 2E). Serum-dependent up-regulation of myeloblastin mRNA was obtained when uninduced HL-60 cells that had been deprived of serum were exposed to medium containing 10% fetal bovine serum (FIG. 2F).

Anti-peptide antibodies react with myeloblastin for identification of expressed myeloblastin. We raised polyclonal antibodies against a 16 amino acid long synthetic peptide (from Val-64 to Ile-78: VFLNNYDA-ENKLNDIL). The peptide sequence was chosen according to the hydropathic profile and the search of a deduced amino acid sequence divergent from all other serine proteases available in the National Biomedical Research Foundation library. Hybrid selection of myeloblastin mRNA was performed using a cDNA sequence (Parnes, et al., 1981) that encompassed the sequence corresponding to the synthetic peptide. In vitro translation of this mRNA resulted in a unique protein of approximately 23 kD (data not shown). The synthetic peptide was used for immunization of rabbits. In HL-60 cells, one serum identified a protein with a molecular mass of approximately 30 kD (FIG. 3A). Despite the fact that the antiserum used throughout our experiments was affinity purified using the synthetic peptide coupled to CH-Sepharose 4B, the signal on immunoblots was always diffuse. This and the fact that the deduced amino acid sequence has a calculated molecular mass of 23.6 kD instead of the approximately 30 kD observed on immunoblots suggest that carbohydrates are added to myeloblastin. Glycosylation of this protease is likely since there are two potential N-linked glycosylation sites (FIG. 1E).

As with its mRNA, myeloblastin is down-regulated after treatment of HL-60 cells with $Me_2SO$, PMA, 1,25-$(OH)_2D_3$, and RA (FIG. 3B) and is undetectable in normal human PBMs (FIG. 3C). As shown by both immunoprecipitation and immunoblotting, the approximately 30 kD band labels strongly with [$^3$H] diisopropylfluorophosphate ([$^3$H]DFP) (FIGS. 3A and 3D), a specific affinity label for serine proteases (Draut, 1977). This [$^3$H]DFP-labeled band disappears after treatment with PMA (FIG. 3D).

Down-Regulation of myeloblastin causes monocytic differentiation and inhibits proliferation of promyelocyte-like leukemic cells. An 18-mer antisense (antisense-mbn) oligodeoxynucleotide 5'-d(CTGGGGTATGTC CCGCAG)-3' (Genebank Accession No. M29142), complementary to a sequence starting at position 94 downstream of the ATG initiation codon (FIG. 1D) of myeloblastin mRNA was synthesized. This sequence had no identity to any known sequence in the National Biomedical Research Foundation library and was used to inhibit translation of myeloblastin mRNA. Northern blot analysis shows that antisense-mbn oligodeoxynucleotide hybridized to a unique mRNA of approximately 1.3 kb that is present in uninduced HL-60 cells but not in HL-60 cells treated with 1,25-$(OH)_2D_3$ for 48 or 120 hours (FIG. 4A). This is consistent with the fact that myeloblastin mRNA disappears after treatment of HL-60 cells with 1,25-$(OH)_2D_3$ (FIG. 2B).

To verify the uptake the antisense-mbn oligodeoxynucleotide by HL-60 cells in tissue culture medium, and the percent uptake was determined as described (Wickstrom, et al., 1986). Approximately 2.2% of the 5'-labeled antisense-mbn oligodeoxynucleotide preparation was associated with the cell pellet after 4 hours (FIG. 4B). A parallel experiment used to study the stability of the intracellular antisense-mbn oligodeoxynucleotide showed that the 18-mer oligodeoxynucleotide was still intact at 24 hours (FIG. 4C).

1F10 cells treated continuously with 1,25-$(OH)_2D_3$ (1F10-D3 cells) are immature, promyelocyte-like, grow exponentially (Cayre, et al., 1987), and express myeloblastin (FIG. 4D) and its mRNA (FIG. 1). These cells were used to study the effects of the antisense-mbn oligodeoxynucleotide on cell proliferation and differentiation. Heterogeneity of the cell population in the nonclonal HL-60 cell line complicates interpretation of the cell cycle analysis (Holt, et al., 1988); in contrast, the fact that 1F10-D3 cells are clonal simplified the interpretation of our data. In 1F10-D3 cells, myeloblastin mRNA is down-regulated (data not shown), and differentiation and growth arrest occur (Cayre, et al., 1987) following exposure to PMA. Under the same conditions, myeloblastin is down-regulated (FIG. 4D). This situation allowed us to explore whether, in 1F10-D3 cells, down-regulation of myeloblastin by antisense-mbn oligodeoxynucleotide would result in inhibition of proliferation and induction of differentiation toward monocyte-like cells.

The antisense-mbn oligodeoxynucleotide was added to 1F10-D3 cells every 8 hours, and aliquots of these cells were collected at intervals up to 12 days. Untreated 1F10-D3 cells (in which myeloblastin mRNA is permanently expressed) as well as 1F10-D3 cells treated under the same conditions and for the same periods of time with a sense oligodeoxynucleotide 5'-d(CTGCGGGACATACCCCAG)-3' (sense-mbn) and a vesicular stomatitis virus (VSV) antisense oligodeoxynucleotide 5'-d(TTGGGATAACACTTA)-3' (antisense-VSV) were uses as negative controls. The antisense-VSV sequence is complementary to nucleotides 17-31 of VSV M-protein mRNA and nonspecifically inhibited translation of VSV mRNAs (Wickstrom, et al., 1986). This antisense-VSV sequence was previously used to control for sequence-specific effects of an anti-c-myc pentadecadeoxynucleotide on HL-60 cell proliferation (Wickstrom, et al., 1988). Inhibition of proliferation of antisense-mbn-treated 1F10-D3 cells was assessed by cell cycle analysis as described (Cayre, et al., 1987), and their differentiation was verified by studying their morphology as well as their expression of complement receptor 3 (CR3). The cells were also analyzed cytochemically for acid α-acetate esterase expression.

By 7 days, antisense-mbn treated 1F10-D3 cells exhibited a marked shift toward a more differentiated morphology as assessed by Giemsa staining (data not shown). After a 10 day exposure of 1F10-D3 cells to antisense-mbn oligodeoxynucleotide, myeloblastin expression was decreased as much as in the same cells treated for the same time with 107 nM of PMA (FIG. 4D). In contrast, the level of myeloblastin expression in 1F10-D3 cells treated for 10 days with either sense-mbn or antisense-VSV oligodeoxynucleotides was as high as in untreated 1F10-D3 cells (FIG. 4D). At day 10, most of the cells treated with antisense-mbn oligodeoxynucleotide had a less basophilic cytoplasm, more cytoplasmic vacuoles, and a decreased nuclear to cytoplasmic ratio compared with cells untreated or treated with either sense-mbn or antisense-VSV oligodeoxynucleotides (FIGS. 5B vs. 5A, 5D, and 5E). These differentiated features increased progressively and, after a 12 day exposure to the antisense-mbn oligodeoxynucleotide, 80% of the cells exhibited morphological characteristics of monocytes, i.e., a decreased nuclear to cytoplasmic ratio, a grayish cytoplasm, segmented nuclei with fine chromatin, and barely visible nucleoli (FIG. 5C). 1F10-D3 cells treated with either sense-mbn or antisense-VSV oligodeoxynucleotides remained morphologically promyelocyte-like and similar to the untreated 1F10-D3 cells (FIGS. 5A, 5D, and 5E). At day 10, about 24% to 31% of antisense-mbn-treated 1F10-D3 cells expressed the differentiation-specific CR3 (FIG. 6A(4), while 1F10-D3 cells untreated or treated with either sense-mbn or antisense-VSV oligodeoxynucleotides remained negative (FIGS. 6A(1), 6A(2), and 6A(3)). Treatment of 1F10-D3 cells with antisense-mbn oligodeoxynucleotide for 10 days resulted in withdrawal of most cells from the cell cycle (12% of the cells remained in the S phase of the cell cycle) and a decrease in RNA content (FIG. 6B(4). 1F10-D3 cells treated 10 days with 107 nM of PMA exhibited comparable withdrawal from the cell cycle (11% of cells remained in the S phase of the cell cycle) and decrease in RNA content (FIG. 6B(5). In contrast, 1F10-D3 cells untreated or treated with either sense-mbn or antisense-VSV oligodeoxynucleotide were growing exponentially (22% of cells were in the S phase) (FIGS. 6B(1), 6B(2), and 6B(3)). Cytochemical studies showed an increase in the number of acid α-acetate esterase positive cells in antisense-mbn-treated 1F10-D3 cells (16%) when compared with 1F10-D3 cells untreated or treated with either sense-mbn or antisense-VSV oligomers (2%, 2%, and 4%, respectively). One difference between antisense-mbn and PMA-mediated differentiation of 1F10-D3 cells was that the cells did not adhere to the tissue culture flask when treated with antisense-mbn.

Discussion

Down-regulation of myeloblastin inhibits proliferation and induces differentiation of promyelocyte-like leukemic cells. Using a subtracted cDNA cloning procedure, we have identified a protease whose down-regulation in promyelocyte-like leukemia cells inhibits their proliferation and induces their differentiation toward monocytoid cells.

A key observation was that myeloblastin mRNA was down-regulated by 1,25-$(OH)_2D_3$ in original HL-60 cells but not in 1F10-D3 cells. We have previously shown that, in contrast to HL-60 cells, 1F10 cells remain blastic and grow exponentially when exposed to 1,25-$(OH)_2D_3$ (Cayre, et al., 1987). We have shown here that treatment of 1F10-D3 cells by PMA resulted in down-regulation of myeloblastin. Using an antisense oligodeoxynucleotide complementary to myeloblastin mRNA, we have shown that inhibition of myeloblastin expression resulted in proliferation arrest and induced differentiation of 1F10-D3 cells.

Regulation of myeloblastin has similarities with regulation of c-myc. A remarkable feature of myeloblastin is that it is down-regulated by both monocytic and granulocytic inducers of HL-60 differentiation. This down-regulation by several inducers is consistent with the fact that this serine protease is associated with proliferation arrest—which always accompanies HL-60 differentiation (Collins, et al., 1977; Huberman and Callagham, 1979; Rovera, et al., 1979; Breitman, et al., 1980; Bar-Shavit, et al., 1983; McCarthy, et al., 1983)—and is reminiscent of the down-regulation of c-myc mRNA during differentiation of HL-60 cells.

Other genes that are regulated during HL-60 differentiation, such as c-myc and c-fos, can be induced in response to serum. Because myeloblastin mRNA is induced in response to serum stimulation of HL-60 cells, we propose that myeloblastin is a member of a restricted family of genes that are associated with proliferation and are regulated during HL-60 differentiation. Since reduction of c-myc expression may not be obligatory or sufficient for growth arrest to occur (Shen-Ong, et al., 1987; Cayre, et al., 1987), it will be of interest to know whether myeloblastin and c-myc are interdependent for controlling proliferation and differentiation of HL-60 cells. It will also be of interest to explore whether similar serum and transcription factors regulate both myeloblastin and c-myc expression.

Elucidating the molecular mechanisms that regulate cellular proliferation and differentiation is critical to understanding leukemogenesis. Our data strongly suggest that myeloblastin is part of a process regulating proliferation and differentiation of HL-60 cells. Whether regulation of myeloblastin expression is restricted to differentiation and growth arrest to leukemic cells or is also involved in cellular differentiation and growth arrest of normal cells is under investigation. We are now exploring the role of myeloblastin in the control of cell proliferation and differention. The fact that down-regulation of a unique serine protease can inhibit proliferation and induce differentiation of promyelocyte-like human leukemic cells raises the possibility of finding a specific protease inhibitor to promote these processes.

References

1. Albert, K. A., Walaas, L. l., Wang, J. K. T., and Greengard P. (1986). Widespread occurrence of "87 kDa," a major specific substrate for protein kinase C. Proc. Natl. Acad. Sci. U.S.A. 83, 2822-2826.
2. Agrawal, S., Ikeuchi, T., Sun, D., Sarin, P. S., Konopka, A., Maizel, J., and Zamecknik, P. C. (October 1989). Inhibition of human immunodeficiency virus in early infected and chronically infected cells by antisense oligodeoxynucleotides and their phosphothioate analogues. Biochemistry 86, 7790-7794.
3. Baker, J. B., Knauer, J. D., and Cunningham, D. D. (1986). Protease nexins: secreted protease inhibitors that regulate protease activity at or near the cell surface. In The Receptors, Vol. III, P.M. Conn, ed. (London: Academic Press), pp. 153-172.
4. Bar-Shavit, Z., Teitelbaum, S. L., Reitsma, P., Hall, A., Peg. L. E., Trial, J., and Khas, A. J. (1983). Induction of monocytic differentiation and bone resorption by 1,25 dihydroxyvitamin $D_3$. Proc. Natl. Acad. Sci. U.S.A. 80, 5907-5911.
5. Bode, W., Wei, A. Z., Huber, R., Meyer, E., Travis, J., and Neumann, S. (1986). X-ray crystal structure of the complex of human leukocyte elastase and the third domain of the turkey ovomucoid inhibitor. EMBO J. 5, 2453-2458.
6. Bolton, A. E., and Hunter, W. M. (1973). The labelling of protein to high specific radioactivity by conjugation to a $^{125}I$-containing acylating agent. Biochem. J. 133, 529-539.
7. Bonner, W. M., and Laskey, R. A. (1974). A film detection method for tritium-labelled proteins and nucleic acids in polyacrylamide gels. Eur. J. Biochem. 46, 83-88.
8. Breitman, T. R., Selonick, S. E., and Collins, S. J. (1980). Induction of differentiation of the human promyelocytic leukemia cell line (HL-60) by retinoic acid. Proc. Natl. Acad. Sci. U.S.A. 77, 2936-2940.
9. Carrell, R. W. (1988). Enter a protease inhibitor. Nature 331, 478-479.
10. Cayre, Y., Raynal, M. C., Darzynkiewicz, Z., and Dorner, M. H. (1987). Model for intermediate steps in monocytic differentiation: c-myc, c-ims, and ferritin as markers. Proc. Natl. Acad. Sci. U.S.A. 84, 7619-7623.
11. Chirgwin, J. M., Przybkyla, A. E., MacDonald, R. J., and Rutter, W. J. (1979). Isolation of biologically active ribonucleic acid from sources enriched in ribonuclease. Biochemistry 24, 5294-5299.
12. Collins, S. J., Gallo, R. C., and Gallagher, R. E. (1977). Continuous growth and differentiation of myeloid leukaemic cells in suspension culture. Nature 270, 347-349.
13. Collins, S. J., Ruscetti, F. W., Gallagher, R. E., and Gallo, R. C. (1978). Terminal differentiation of human promyelocytic leukemia cells induced by dimethyl sulfoxide and other polar compounds. Proc. Natl. Acad. Sci. U.S.A. 75, 2458-2462.
14. Darzynkiewicz, Z., Williamson, B., Carswell, E. A., and Old, L. J. (1984). Cell cycle-specific effects of tumor necrosis factor. Cancer Res. 44, 83-90.
15. Einat, M., Resnitzky, D., and Kimchi, A. (1985). Close link between reduction of c-myc expression by interferon and $G_0/G_1$ arrest. Nature 313, 597-600.
16. Engvall, E. (1980). Enzyme immunoassay ELISA and EMIT. Meth. Enzymol. 70, 419-439.
17. Fleit, H. B., Wright, S. D., Durie, C. J., Valinsky, J. E., and Unkeless, J. C. (1984). Ontogeny of Fc receptors and complement receptor (CR3) during human myeloid differentiation. J. Clin. Invest. 73, 516-525.
18. Geliebter, J., Zeff, R. A., Melvoid, R. W., and Nathenson, S. G. (1986). Mitotic recombination in germ cells generated two major histocompatibility complex mutant genes shown to be identical by RNA sequence analysis: $K^{bm9}$ and $K^{bm4}$. Proc Natl. Acad. Sci. U.S.A. 83, 3371-3375.
19. Gibson, W. H., Burack, S. L., and Picciano, A. (1984). The effects of serine protease inhibitors on morphological differentiation of murine neuroblastoma cells (NB15). J. Cell. Physiol. 119, 119-126.
20. Gloor, S., Odink, K., Guenther, J., Nick, H., and Monard, D. (1986). A glia-derived neurite promoting factor with protease inhibitory activity belongs to the protease nexins. Cell 47, 687-693.
21. Hanahan, D. (1983). Studies on transformation of *Escherichia coli* with plasmids. J. Mol. Biol. 166, 557-580.
22. Hartley, B. S. (1970). Homologies in serine proteases. Phil. Trans. Roy. Soc. (Lond.) B 257, 77-87.
23. Heikkila, R., Schwab, G., Wickstrom, E., Loke, S. L., Pluznik, D. H., Watts, R., and Neckers, L. M. (1987). A c-myc antisense oligodeoxynucleotide inhibits entry into S phase but not progress from $G_0$ to $G_1$. Nature 328, 445-449.
24. Hofer, E., and Darnell, J. E., Jr. (1981). The primary transcription unit of mouse $\beta$-major globin gene. Cell 23, 585-593.
25. Holt, J. T., Redner, R. L., and Nienhuis, A. W. (1988). An oligomer complementary to c-myc mRNA inhibits proliferation of HL-60 promyelocytic cells and induces differentiation. Mol. Cell. Biol. 8, 963-973.

26. Huberman, E., Callagham, M. F. (1979). Induction of terminal differentiation in human promyelocytic leukemia cells by tumor promoting agents. Proc. Natl. Acad. Sci. U.S.A. 76, 1293–1297.
27. Kaczmarek, L., Hyland, J., Watt, R., Rosenberg, M., and Baserga, R. (1985). Microinjected c-myc as a competence factor. Science 228, 1313–1315.
28. Kelly, K., Cochran, B., Stiles, C., and Leder, P. (1983). Cell-specific regulation of the c-myc gene by lymphocyte mitogens and platelet-derived growth factor. Cell 35, 603–610.
29. Koeffler, H. P. (1983). Induction of differentiation of human acute myelogenous leukemia cells: therapeutic implications. Blood 62, 709–721.
30. Kozak, M. (1984). Point mutations close to the AUG initiator codon affect the efficiency of translation of preproinsulin in vitro. Nature 308, 241–246.
31. Kraut, J. (1977). Serine proteases: Structure and mechanism of catalysis. Ann. Rev. Biochem. 46, 331–358.
32. Laemmli, U. K. (1970). Cleavage of structural proteins during the assembly of the head of bacteriophage T4. Nature 227, 680–685.
33. Land, H., Grez, M., Hauser, H., Lindenmaier, W., and Shutz. G. (1981). 5' terminal sequence of eucaryotic mRNA can be cloned with high efficiency. Nucl. Acids Res. 9, 2251–2267.
34. Lerner, R. A., Green, N., Alexander, H., Liu, F. T., Sutcliffe, J. G., and Shinnick, T. M. (1981). Chemically synthesized peptides predicted from the nucleotide sequence of the hepatitis B virus genome elicit antibodies reactive with the native envelope of Dane particles. Proc. Natl. Acad. Sci. U.S.A. 78, 3402–3407.
35. Lipman, D. J., and Pearson, W. R. (1985). Rapid and sensitive protein similarity searches. Science 227, 1435–1441.
36. McCarthy, D. M., San Miguel, J., Freake, H. C., Green, P. M., Zola, H., Catowsky, D., and Goldman, J. (1983). 1,25-dihydroxyvitamin $D_3$ inhibits proliferation of human promyelocytic leukemia (HL-60) cells and induces monocyte-macrophage differentiation in HL-60 and normal human bone marrow cells. Leuk. Res. 7, 51–55.
37. Mitchell, R. L., Zokas, L., Schreiber, R. D., and Verma, I. M. (1985). Rapid induction of the expression of proto-onocogene fos during human monocytic differentiation. Cell 40, 209–217.
38. Mueller, J., Brun Del Re, G., Buerki, H., Keller, H. V., Hess, M. W., and Cottier, H. (1975). Nonspecific acid esterase activity: a criterion for differentiation of T and B lymphocytes in mouse lymph nodes. Eur. J. Immunol. 5, 270–274.
39. Muller, R., Curran, T., Muller, D., and Guilbert, L. (1985). Induction of c-fos during myelomonocytic differentiation and macrophage proliferation. Nature 314, 546–548.
40. Mushinski, J. F., Blattner, F. R., Owens, J. D., Finkelman, F. D., Kessler, S. W., Fitsmaurice, L, Potter, M., and Tucker, P. W. (1980). Mouse immunoglobulin D: construction and characterization of a cloned delta chain cDNA. Proc. Natl. Acad. Sci. U.S.A. 77, 7405–7409.
41. Parnes, J. R., Velan, B., Felsenfeld, A., Ramanathan, J., Ferrini, U., Appella, E., and Seidman, J. G. (1981). Mouse $\beta_2$-microglobulin cDNA; a screening procedure for cDNA clones corresponding to rare mRNAs. Proc. Natl. Acad. Sci. U.S.A. 78, 2253–2257.
42. Pasternack, M. S., and Eisen, H. N. (1985). A novel serine esterase expressed by cytotoxic T lymphocytes. Nature 314, 743–745.
43. Reitsma, P. H., Rothberg, P. G., Astrin, S. M., Trial, J., Bar-Shavit, Z., Hall, A., Teitelbaum, S. L. and Kahn, A. J. (1983). Regulation of myc gene expression in HL-60 leukaemia cells by a vitamin D metabolite. Nature 306, 492–494.
44. Rovera, G., Santoli, D., and Damsky, C. (1979). Human promyelocytic leukemia cells in culture differentiate into macrophage-like cells when treated with a phorbol diester. Proc. Natl. Acad. Sci. U.S.A. 76, 2779–2783.
45. Rowekamp, W., and Firtel, R. A. (1980). Isolation of developmentally regulated genes from Dictyostelium. Dev. Biol. 79, 409–418.
46. Sanger, F., Nicklen, S., and Coulson, A. R. (1977). DNA sequencing with chain-terminating inhibitors. Proc. Natl. Acad. Sci. U.S.A. 74, 5463–5467.
47. Sariban, E., Mitchell, T., and Kufe, D. (1985). Expression of the c-fms proto-oncogene during human monocytic differentiation. Nature 316, 64–66.
48. Shen-Ong, G., Holmes, K. L. and Morse, H. C. (1987). Phorbol ester-induced growth arrest of murine myelomonocytic leukemic cells with virus-disrupted myb locus is not accompanied by decreased myc and myb expression. Proc. Natl. Acad. Sci. U.S.A. 84, 199–203.
49. Siebenlist, U., Bressler, P., and Kelly, K. (1988). Two distinct mechanisms of transcriptional control operate on c-myc during differentiation of HL-60 cells. Mol. Cell. Biol. 8, 867–874.
50. Solomon, D. H., Raynal, M. -C. Tejwani, G. A., and Cayre, Y. E. (1988). Activation of the fructose 1,6-bisphosphatase gene by 1,25-dihydroxy-vitamin $D_3$ during monocytic differentiation. Proc. Natl. Acad. Sci. U.S.A. 85, 6904–6908.
51. Simpson, R. U., Hsu, T., Begley, D. A. Mitchell, B. S., and Alizadeh, B. N. (1987). Transcriptional regulation of the c-myc proto-onocogene by 1,25-dihydroxyvitamin $D_3$ in HL-60 promyelocytic leukemia cells. J. Biol. Chem. 262, 4101–4108.
52. Suggs, S. V., Wallace, R. B., Hirose, T., Kawashima, E. H., and Itakura, K. (1981). Use of synthetic oligonucleotides as hybridization probes: isolation of cloned cDNA sequences for human $\beta_2$ microglobulin. Proc. Natl. Acad. Sci. U.S.A. 78, 6613–6617.
53. Sullivan, L. M., and Quigley, J. P. (1986). An anticatalytic monoclonal antibody to avian plasminogen activator: its effects on behavior of RSV-transformed chick fibroblasts. Cell 45, 905–915.
54. Takahashi, H., Nukiva, T., Basset, P., and Crystal, R. G. (1988). Myelomonocytic cell lineage expression of the neutrophil elastase gene. J. Biol. Chem. 263, 2543–2547.
55. Tanzi, R. E., McClatchey, A. L., Lamperti, E. D., Villa-Komaroff, L., Gusella, J. F., and Neve, R. L. (1988). Protease inhibitor domain encoded by an amyloid protein precursor mRNA associated with Alzheimer's disease. Nature 331, 528–530.
56. Towbin, H., Staehelin, T., and Gordon, J. (1979). Electrophoretic transfer of proteins from polyacrylamide gels to nitrocellulose sheets: procedure and some applications. Proc. Natl. Acad. Sci. U.S.A. 76, 4350–4354.

57. Westin, E. H., Wong-Staal, F., Gelmann, E. P., Dally Favera, R., Papas, T. S., Lautenberger, J. A., Eva, A., Reddy, E., Tronick, S. R., Aaronson, S. A., and Gallo, R. C. (1982). Expression of cellular homologues of retroviral onc genes in human hematopoietic cells. Proc. Natl. Acad. Sci. U.S.A. 79, 2490-2494.

58. Wickstrom, E., Simonet, W. S., Medlock, K., and Ruiz-Robles, I. (1986). Complementary oligonucleotide probes of vesicular stomatitis virus matrix protein mRNA translation. Biophys. J. 49, 15-17.

59. Wickstrom, E. L., Bacon, T. A., Gonzales, A., Freeman, D. E., Lyman, G. H., and Wickstrom, E. (1988). Human promyelocytic leukemia HL-60 cell proliferation and c-myc protein expression are inhibited by an antisense pentadecadeoxynucletide targeted against c-myc mRNA. Proc. Natl. Acad. Sci. U.S.A. 85, 1028-1032.

60. Wickstrom, E. L., Bacon, T. A., Gonzalez, A., Lyman, G. H., and Wickstrom, E. (March, 1989). Anti-c-myc DNA increases differentiation and decreases colony formation by HL-60 cells. In Vitro Cell. and Devel. Biol., 24, 297-302.

61. Wright, S. D., Rao, P. E., Van Voorhis, W. C., Craigmyle, L. S., Kyoto, I., Talle, M. A., Westberg, E. F., Golstein, G., and Silverstein, S. C. (1983). Human neutrophil Fc receptor distribution and structure. Proc. Natl. Acad. Sci. U.S.A. 79, 3275-3279.

What is claimed is:

1. An isolated nucleic acid molecule encoding a myeloblastin and having a coding sequence comprising the coding sequence shown in FIG. 1D.
2. An isolated DNA molecule of claim 1.
3. An isolated cDNA molecule of claim 2.
4. An isolated RNA molecule of claim 1.
5. An isolated nucleic acid molecule of claim 1 wherein the myeloblastin is human myeloblastin.
6. A cDNA molecule of claim 5.
7. An antisense oligonucleotide which is at least 15 nucleotides in length having a sequence complementary to a nucleic acid molecule encoding myeloblastin as shown in FIG. 1D.
8. A nucleic acid probe comprising an antisense oligonucleotide of claim 7 labelled with a detectable marker.
9. A nucleic acid probe of claim 8 wherein the detectable marker is selected from the group consisting of a radiolabelled molecule, a fluorescent molecule, an enzyme, or a ligand.
10. The nucleic acid probe of claim 9 wherein the nucleic acid is DNA.
11. The nucleic acid probe of claim 9 wherein the nucleic acid is RNA.
12. The antisense oligonucleotide of claim 7 having a sequence complementary to myeloblastin mRNA.
13. An oligonucleotide of claim 12 having the sequence 5'-d(CTGGGGTATGTCCCGCAG)-3'.

* * * * *